United States Patent [19]
Rothman et al.

[11] Patent Number: 6,004,944
[45] Date of Patent: *Dec. 21, 1999

[54] PROTEIN DELIVERY BY SECRETORY GLAND EXPRESSION

[75] Inventors: Stephen S. Rothman, Berkeley; Ira D. Goldfine, Kentfield; Michael S. German, San Francisco, all of Calif.

[73] Assignee: The Regents of the University of California, Oakland, Calif.

[ * ] Notice: This patent is subject to a terminal disclaimer.

[21] Appl. No.: 08/942,939

[22] Filed: Oct. 2, 1997

Related U.S. Application Data

[63] Continuation-in-part of application No. 08/591,197, Jan. 16, 1996, Pat. No. 5,885,971, which is a continuation-in-part of application No. 08/410,660, Mar. 24, 1995, Pat. No. 5,837, 693.

[51] Int. Cl.$^6$ .............................. A61K 48/00; C12N 15/00
[52] U.S. Cl. ..................... 514/44; 562/23.1; 435/320.1; 435/325; 435/455; 435/458
[58] Field of Search ..................... 514/44; 424/93.21; 435/325, 320.1, 455, 458; 536/23.1

[56] References Cited

U.S. PATENT DOCUMENTS

| | | | |
|---|---|---|---|
| 4,394,443 | 7/1983 | Weissman et al. | 435/6 |
| 4,683,195 | 7/1987 | Mullis et al. | 435/6 |
| 4,683,202 | 7/1987 | Mullis | 435/6 |
| 4,861,719 | 8/1989 | Miller | 435/236 |
| 5,139,941 | 8/1992 | Muzyczka et al. | 435/455 |
| 5,219,740 | 6/1993 | Miller et al. | 435/69.6 |
| 5,240,846 | 8/1993 | Collins et al. | 435/325 |
| 5,292,662 | 3/1994 | Sandymeyer | 435/325 |
| 5,328,470 | 7/1994 | Nabel et al. | 604/101 |
| 5,356,806 | 10/1994 | Harris et al. | 435/325 |
| 5,399,346 | 3/1995 | Anderson et al. | 424/93.21 |
| 5,521,291 | 5/1996 | Curiel et al. | 530/391.7 |
| 5,561,165 | 10/1996 | Lautt et al. | 514/667 |
| 5,589,466 | 12/1996 | Felgner et al. | 514/44 |
| 5,674,192 | 10/1997 | Sahatjian et al. | 604/28 |
| 5,681,744 | 10/1997 | Greenstein | 435/320.1 |
| 5,786,340 | 7/1998 | Henning et al. | 514/44 |
| 5,792,751 | 8/1998 | Ledley et al. | 514/44 |
| 5,830,878 | 11/1998 | Gorman et al. | 514/44 |
| 5,836,905 | 11/1998 | Lemelson et al. | 604/21 |

FOREIGN PATENT DOCUMENTS

WO 94/26915  11/1994  WIPO .

OTHER PUBLICATIONS

Nicou et al., Biol. Cell, vol. 47, 121–130, 1983.
Yang et al., PNAS, vol. 90, pp. 4601–4605, 1993.
Papp, et al., *Acta. Physiol. Acad. Sci. Hung.,* 56(4):401–410 (1980).
Amsterdam, et al., "Studies on Dispersed Pancreatic Exorcine Cells," *J. Cell. Biol.* 63:1057–1073 (1974).
Avery, et al., "Studies on the Chemical Nature of the Substance Inducing Transformation of Pneumococcal Types," *J. Exp. Med.,* 79:137–158 (1944).
Baum, B.J., "Advances in Salivary and Soft Tissue Management", *JADA* 125:26S–30S (1994).
Boshart, et al., "A Very Strong Enhancer is Located Upstream of an Immediate Early Gene of Human Cytomegalovirus," *Cell,* 41:521–530.
Brody, S.I. and Crystal, R.G., "Adenovirus–Mediated in Vivo Gene Transfer", *N.Y. Acad. Sci.* 716:90–101 (1994).
Cockell, et al., "Identification of a Cell–Specific DNA–Binding Activity that Interacts with a Transcriptional Activator of Genes Expressed in the Acinar Pancreas," *Mol. Cell. Biol.,* 9:2464–2476 (1989).
Coghlan, A., "Gene Dream Fades Away," *New Scientist,* 14–15 (Nov. 1995).
Crystal, R.G., "Transfer of Genes to Humans: Early Lessons and Obstacles to Success," *Science,* 270:404–410 (1995).
Elango, et al., "Molecular Cloning and Characterization of Six Genes, Determination of Gene Order and Intergenic Sequences and Leader Sequence of Mumps Virus," *J. Gen. Virol.,* 69:2893–2900 (1988).
Felgner, et al., Lipofection: A Highly Efficient, Lipid–Mediated DNA Transfection Procedure, *Proc. Nat'l. Acad. Sci. U.S.A.,* 84:7413–7417 (1987).
Fynan, et al., "DNA Vaccines: Protective Immunizations by Parenteral, Mucosal and Gene–Gun Innoculants," *Proc. Nat'l. Acad. Sci. U.S.A.,* 90:11478–11482 (1993).
Gerrard, et al., "Towards Gene Therapy for Haemophilia B Using Primary Human Keratinocytes," *Nat. Genet.,* 3:180 (1993).
Gitschier, et al., "Characterization of the Human Factor VIII Gene," *Nature,* 312:326–330 (1984).
Gorman, et al., "The Rous Sarcoma Virus Long Terminal Repeat is a Strong Promoter when Introduced into a Variety of Eukaryotic Cells by DNA–Mediated Transfection," *Proc. Nat'l. Acad. Sci. U.S.A.* 79:6777–6781 (1982).
Grendell, J.H. and Rothman, S.S., "Effect of changes in circulating amylase levels on amylase output in bile", *The American Physiological Society* G54–G59 (1982).
Groot, et al., "The Himan α–Amylase Multigene Family Consists of Haplotypes with Variable Numbers of Genes," *Genomics,* 5:29–42 (1989).

(List continued on next page.)

*Primary Examiner*—Scott D. Priebe
*Assistant Examiner*—Dave Trong Nguyen
*Attorney, Agent, or Firm*—Carol L. Francis; Bozicevic, Field & Francis, LLP

[57] ABSTRACT

Secretory gland cells, particularly pancreatic, hepatic, and salivary gland cells, are genetically altered to operatively incorporate a gene which expresses a protein which has a desired therapeutic effect on a mammalian subject. The expressed protein is secreted directly into the bloodstream to obtain therapeutic levels of the protein thereby treating the patient in need of the protein. The transformed secretory gland cells provide long term or short term therapies for diseases associated with a deficiency in a particular protein or which are amenable to treatment by overexpression of a protein.

31 Claims, 18 Drawing Sheets

OTHER PUBLICATIONS

Gunzburg et al., *Molecular Medicine Today*, 410–417 (1995).

Hagenbuchle, et al., "Expression of Mouse Amy-2$^a$ Alpha–amylase Genes is Regulated by Strong Pancreas–Specific Promoters," *J. Mol. Biol.*, 185:285–293 (1985).

Hewitt, et al., "Human Gastric Intrinsic Factor: Characterization of cDNA and Genomic Clones and Localization to Human Chromosome 11," *Genomics*, 10:432–440 (1991).

Jones, et al., "A Salivary Amylase Transgene is Efficiently Expressed in Liver but Not in Parotid Gland of Transgenic Mice," *Nucleic Acids Res.*, 17(6):6613–6623 (1989).

Korman, et al., "Expression of Human Class II Major Histocompatibility Complex Antigens using Retrovirus Vectors," *Proc. Nat'l. Acad. Sci. U.S.A.*, 84:2150–2154 (1987).

Kwano, et al., "Complete Nucleotide Sequence of the Matrix Gene of Human Parainfluenza Type 2 Virus and Expression of the M Protein in Bacteria," *Virol.* 179:857–861 (1990).

Ledley, Human Gene Therapy, 6:1129–1144 (1995).

Lowery, et al., "Protein Measurement with the Folin Phenol Reagent," *J. Biol. Chem.*, 193:265–275 (1951).

Maeda, H., et al., "Adenovirus–Mediated Transfer of Human Lipase Complementary DNA to the Gallbladder", *Gastroentererology* 106:1638–1644 (1994).

Marshall, *Science*, 269:1050 (1995).

Marshall, "Less Hype, Mor Biology Needed for Gene Therapy," *Science*, 270: 1751 (Dec. 1995).

Martial, et al., "Human Growth Hormone: Complimentary DNA Cloning and Expression in Bacteria," *Biotechnology* 24:293–298 (1992).

Mastrangeli, A. et al., "Direct in vivo adenovirus–mediated gene transfer to salivary glands." *Am. J. Physiol.* 266(6, part 1):G1146–55 (1994).

Mastrangelo et al., "Gene Therapy for Human Cancer: An Essay for Clinicians," *Seminars in Oncology*, 23(1):4–21 (1996).

Miyasaka, K., and Rothman, S., "Endocrine secretion of α–amylase by the pancreas", *American Physiological Society* G170–G175 (1981).

Morgan, et al., "Expression of an Exogenous Growth Hormone by Transgenic Human Epidermal Cells," *Science*, 237:1476–1479 (1987).

Morsey, et al., "Progress Toward Human Gene Therapy," *JAMA*, 270:2338–2345 (1993).

Mulligan, R.C., "The Basic Science of Gene Therapy", *Science* 260:926–932 (1993).

Newgard, C.B. et al., "Molecular engineering of the pancreatic β–cell", *J. Lab. Clin. Med.* 122(4):356–363 (1993).

Orkin, et al., Report and Recommendation of the Panel to Assess the NIH Investment in Research on Gene Therapy, (1995).

Pittet, et al., "Mouse Alpha–amylase Loci, Amy–1$^a$ and Amy–2$^a$, are Closely Kinked," *J. Mol. Biol.*, 182:359–365 (1985).

Ramakrishna, J. and Grand, R.J., "Gene Therapy for Exocrine Pancreatic Insufficiency", *Gastroenterology* 106(6):1711–1713 (1994).

Robbins, et al. "Retrotransposons and the Evolution of Mammalian Gene Expression," *Genetica*, 86:191–201 (1992).

Rosenfeld, et al., "Adenovirus–Mediated Transfer of a Recombinant αl–Antitrypsin Gene to the Lung Epithlieum In Vivo," *Science*, 252:431–434 (1991).

Rosenfeld, et al., "In–Vivo Transfer of the Human Cystic Fibrosis Transmembrane Conductance Regulator Gene to the Airway Epithelium," *Cell*, 68:143–155 (1992).

Samara, G. et al., "Molecular Biology and Therapy of Disease", *The American Journal of Surgery* 165:720–727 (1993).

Samuelson, et al., "Expression of the Human Amylase Genes: Recent Origin of a Salivary Amylase Promoter from an Actin Pseudogene," *Nucleic Acids Res.*, 16:8261–8276 (1988).

Schibler, et al., "Structural Arrangement and Tissue–Specific Expression of the Two Murine Alpha–amylase Loci Amy–1 and Amy–2," *Oxf. Surv. Eukaryot. Genes*, 3:210–234 (1986).

Sierra, et al., "Different Tissue–Specific Expression of the Amylase Gene Amy–l in Mice and Rats," *Mol Cell. Biol.* 6(11):4067–4076 (1986).

Suggs, et al., "Use of synthetic Oligonculeotides as Hybridization Probes: Isolation of Cloned cDNA Sequences for Human $β_2$–microglobulin," *Proc. Nat'l. Acad. Sci. U.S.A.* 78:6613–6617 (1981).

Takeuchi, et al., "In Vitro Transcription and Replication of of the Mumps Virus Genome," *Archiv. Virol.*, 128:177–183 (1993).

Tanabayashi, et al., "Expression of Mumps Virus Glycoproteins in Mammalian Cells Cloned form cDNA's: Both F and HN Proteins are Required for Cell Fusion," *Virol.*, 187:801–804 (1992).

Tanabayashi, et al., "Identification of an Amino Acid that Defines the Fusogenicity of Mumps Virus," J. Virol., 67:2928–2931 (1993).

Tariguchi, et al., J. Surgical Res., 70:41–45 (1997).

Ting, et al., "Endogenous Retroviral Sequences are Required for Tissue–Specific Expression of a Human Salivary Amylase Gene," *Genes Dev.*, 6:1457–1465 (1992).

Tomita, et al., "A Novel Type of Human α–Amylase Produced in Lung Carcinoid Tumor," *Gene*, 76:11–18 (1989).

Towbin, et al., "Electrophoretic Transfer of Proteins from Polyacrylamide Gels to Nitrocellulose Sheets: Procedure and Some Applications," *Proc. Nat'l. Acad. Sci. U.S.A.* 76:4350–4354 (1979).

Vile, et al., *Targeted Gene Therapy*, 9:190–199.

Wolff, et al., "Direct Gene Transfer into Mouse Muscle In Vivo," *Science*, 247:1465–1468 (1990).

Wood, et al., "Expression of Active Human Factor VIII from Recombinant DNA Clones," *Nature*, 312:330–337 (1984).

Yang, et al., "In Vivo and In Vitro Gene Transfer to Mammalian Somatic Cells by Particle Bombardment," *Proc. Nat'l. Acad. Sci. U.S.A.*, 87:9568–9572 (1990).

Adesanya, et al., "Immediate Inflammatory Responses to Adenovirus–Mediated Gene Transfer in Rat Salivary Glands," *Human Gene Therapy*, 7:1085–1093 (Jun. 10, 1996).

Barka, et al., "Retrovirus–Mediated Gene Transfer into Salivary Glands In Vivo,"*Human Gene Therapy*, 7:613–618 (Mar. 20, 1996).

Buckel, et al., *TiPS*, 17:450 (1996).

Curiel, et al., *Am. J. Respir. Cell. Mol. Biol.*, 6(3):247–252 (1992).

Friedmann, *Nature Med.*, 2:144 (1996).

Geokas, et al., Am. J. Physiol., 238:238–246 (1980).

Hahn, et al., "Phentypic Correction of Dwarfism by Constitutive Expression of Growth Hormone," *Endocrinology*, 137(11):4988–4993 (1996).

Isenman, et al., "Transport of α–Amylase Across the Basolateral Membrane of the Pancreatic Acinar Cell," *Proc. Nat'l. Acad. Sci. U.S.A.,* 74(9):4068–4072 (1977).

Kagami, et al., "Evidence for the Systemic Delivery of a Transgene Product from Salivary Glands," *Human Gene Therapy,* 7:2177–2184 (Nov. 10, 1996).

Kolodka, et al., "Gene Therapy for Diabetes in Mellitus in Rats by Hepatic Expression of Insulin," *Proc. Nat'l. Acad. Sci. U.S.A.,* 92:3293–3297 (Apr., 1995).

O'Connell, et al., "Facilitated DNA Transfer to Rat Submandibular Gland In Vivo and GRP–Ca Gene Regulation," *Am. J. Physiol.,* 268:G1074–G1078 (1995).

O'Connell, et al., "Transfer of a Gene Encoding the Anti-candidal Protein Histatin 3 to Salivary Glands," *Human Gene Therapy.,* 7:2255–2261 (Dec. 1, 1996).

Papp, et al., *Acta. Physiol. Acad. Sci. Hung.,* 56:4068–4072 (1997).

Raper, et al., "Adenovirus–Mediated In Vivo Gene Transfer and Expression in Normal Rat Pancreas," *Pancreas,* 12(4):401–410 (1996).

Saito, et al., *Jpn. J. Physiol.* 23:477–95 (1973).

Stewart, et al., "Insulin Delivery by Somatic Cell Gene Therapy," *Journal of Molecular Endocrinology,* 11:335–341 (1993).

PROTEIN DELIVERY BY SECRETORY GLAND EXPRESSION

CROSS-REFERENCE TO RELATED APPLICATIONS

This application is a continuation-in-part of U.S. application Ser. No. 08/591,197, filed Jan. 16, 1996, now U.S. Pat. No. 5,885,971 which is a continuation-in-part of U.S. application Ser. No. 08/410,660, filed Mar. 24, 1995, now U.S. Pat. No. 5,837,693, each of which are incorporated herein by reference.

FIELD OF THE INVENTION

This invention relates generally to the field of genetic transformation of cells in vivo, more particularly to in vivo transformation of secretory gland cells by introduction of the transforming nucleic acid into a secretory gland via a secretory gland duct.

BACKGROUND OF THE INVENTION

The ability to replace defective or absent genes has attracted wide attention as a method to treat a variety of human diseases (Crystal 1995 Science 270:404), Lever et al. 1995 Gene Therapy. Pearson Professional, New York p. 1–91; Friedmann 1996 Nature Med. 2:144). Although originally intended as a means of correcting inherited disorders in certain populations of somatic cells, gene-based therapy can be a useful means to supply exogenous gene products to the circulatory system for the treatment of a wide range of systemic disorders that involve deficiencies in circulating proteins, such as hormones, growth factors, and clotting proteins (Lever et al. 1995 supra; Buckel 1996 TiPS 17:450), as well as a means of administering other polypeptide drugs. The success of this application depends upon developing effective methods to both manufacture the desired protein in vivo and then secrete it into blood (Crystal 1995 supra; Lever et al. 1995 supra).

Currently, DNA-based therapy (i.e., gene therapy) is carried out in a variety of ways but involves two general protocols. In the first method, referred to as ex vivo gene therapy, cells are extracted from an individual and subjected to genetic manipulation. After genetic material has been properly inserted into the cells, the cells are implanted back into the individual from which they were removed. Persistent, in vivo expression of the newly implanted genetic material after transplantation of the transformed cells has been successful (see Morgan et al., *Science* 237:1476 (1987); and Gerrard et al., *Nat. Genet.* 3:180 (1993)). In the second approach to DNA-based therapy, referred to as in vivo gene therapy, cells within a living organism are transformed in situ with exogenous genetic material.

Several different methods for transforming cells can be used in accordance with either the ex vivo or in vivo transfection procedures. For example, various mechanical methods can be used to deliver the genetic material, including the use of fusogenic lipid vesicles (liposomes incorporating cationic lipids such as lipofection; see Felgner et al., *Proc. Nat. Acad. Sci. U.S.A.* 84:7413–7417 (1987)); direct injection of DNA (Wolff, et al., *Science* (1990) 247:1465–1468); and pneumatic delivery of DNA-coated gold particles with a device referred to as the gene gun (Yang et al., *Proc. Natl. Acad. Sci. U.S.A.* 1990; 87:1568–9572). Morsy et al. reviews several of the different techniques useful in transformation of cells ex vivo or in vivo and provides citations of numerous publications in each area (Morsy et al., *JAMA* 270:2338–2345 (1993)).

One method of particular interest for delivery of genetic material involves use of recombinant viruses to infect cells in vivo or ex vivo. In these methods, a virus containing the desired genetic material is allowed to infect target cells within the subject. Upon infection, the virus injects its genetic material into the target cells. The genetic material is then expressed within the target cell, providing for expression of the desired genetic material. However, it would be preferable to avoid introduction of the desired genetic material by viral infection for a number of reasons. For example, viral infection results in delivery of viral DNA in addition to the desired genetic material, which may in turn result in undesirable cellular effects such as, adverse immune reactions, productive viral replication, and adverse integration events.

There is a need in the field for a method for delivery of genetic material into a cell in vivo to provide for expression of the introduced polynucleotide and secretion of the gene product it encodes into the bloodstream. The present invention addresses this problem.

SUMMARY OF THE INVENTION

Secretory gland cells are genetically altered to operatively incorporate a gene which is expressed by the genetically altered secretory gland cell to produce a polypeptide which is subsequently secreted into the bloodstream. Specifically, the invention involves introduction of a nucleotide of interest into a secretory gland via the duct system (e.g., by retrograde ductal administration) to transform a secretory gland cell.

In one embodiment the invention features genetic alteration of cells of two secretory glands (e.g., the liver and the pancreas).

In another embodiment, the invention features transformation of pancreatic cells with insulin-encoding nucleic acid to provide for expression and secretion of insulin at levels sufficient to maintain a substantially euglycemic state in a subject having a diabetic syndrome.

A primary object is to provide a non-invasive method of protein delivery (i.e., the method involves introduction of the nucleic acid of interest from outside the body (i.e., from the duct system of particular glands) wherein cells of a secretory gland, preferably the pancreas, salivary gland, or liver of a mammal are genetically modified to express a biologically active and therapeutically useful polypeptide, which polypeptide is secreted into the circulatory system of the individual.

Another object is to produce genetically transformed secretory gland cells which cells have incorporated into their genome genetic material which, when expressed, produces a biologically active and therapeutically useful protein which is secreted into the circulatory system.

An advantage of the present invention is that both long and short term therapy can be provided for diseases wherein individuals are suffering from the disease due to a deficiency in a particular protein, or by supplying an exogenous protein having a desired activity (e.g, antimicrobial activity).

These and other objects, advantages and features of the present invention will become apparent to those persons skilled in the art upon reading the details of the methodology and compositions as more fully set forth below.

DESCRIPTION OF THE PREFERRED EMBODIMENTS

Figure 1:
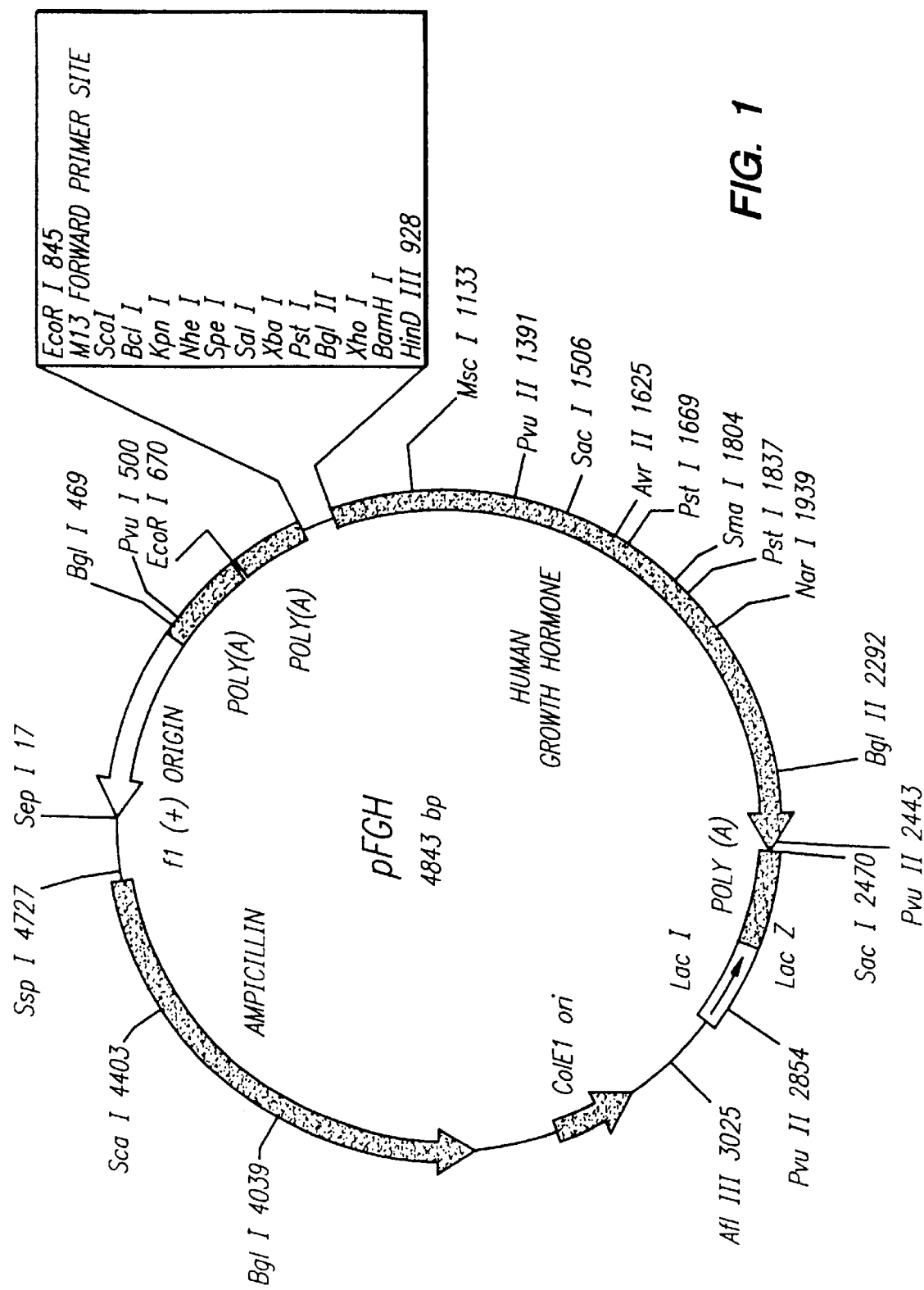
FIG. 1 is a map of the pFGH construct, which contains the human growth hormone (hGH) genomic sequence.

Before the present method of genetically transforming secretory gland cells and methods for protein delivery are described, it is to be understood that this invention is not limited to the particular methodology, protocols, cell lines, secretory glands, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a secretory gland cell" includes a plurality of such cells and reference to "the transformation vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

Definitions

By "secretory gland" is meant an aggregation of cells specialized to secrete or excrete materials not related to their ordinary metabolic needs. Secretory glands include salivary glands, pancreas, mammary glands, thyroid gland, thymus gland, pituitary gland, liver, and other glands well known in the art.

By "exocrine gland" is meant a ducted gland or portion of a ducted gland that releases its products externally relative to the body, e.g., either into the internal cavities such as the ocular and nasal cavities, the lumen of the gastrointestinal tract, or onto the surface of the body.

By "salivary gland" is meant a gland of the oral cavity which secretes saliva, including the glandulae salivariae majores of the oral cavity (the parotid, sublingual, and submandibular glands) and the glandulae salivariae minores of the tongue, lips, cheeks, and palate (labial, buccal, molar, palatine, lingual, and anterior lingual glands).

By "pancreas" is meant a large, elongated, racemose gland situated transversely behind the stomach, between the spleen and the duodenum. The pancreas is composed of an endocrine portion (the pars endocrina) and an exocrine portion (the pars exocrina). The pars endocrina, which contains the islets of Langerhans, produces and secretes proteins, including insulin, directly into the bloodstream. The pars exocrina contains secretory units and produces and secretes a pancreatic juice, which contains enzymes essential to protein digestion, into the duodenum.

By "retrograde ductal injection" is meant the administration of a liquid or other material into the fluid contents of the duct system of an exocrine gland in a direction opposite to the normal flow of that fluid, either at the external orifice of the duct system or through its wall. "Retrograde ductal injection" can be a single, discontinuous administration or continuous administration (i.e., perfusion).

By "transformation" is meant a genetic change induced in a cell following incorporation of new DNA (i.e., DNA exogenous to the cell). Where the cell is a mammalian cell, the genetic change may be achieved by introduction of the DNA into the genome of the cell.

By "transfection" is meant the transformation of a cell with DNA from a virus.

By "transformed cell" is meant a cell into which (or, where the introduced DNA is incorporated into the genome, into an ancestor of which) has been introduced, by means of recombinant DNA techniques, a DNA molecule encoding a protein of interest.

By "nucleic acid of interest" is meant any DNA or RNA molecule which encodes a polypeptide or other molecule which is desirable for administration to a mammalian subject for expression of the product encoded by the nucleic acid of interest and delivery of the encoded product into the blood stream of the mammalian subject. The nucleic acid is generally operatively linked to other sequences which are needed for its expression such as a promoter. The term "DNA of interest" is used as shorthand herein to refer to the nucleic acid of interest.

By "construct" is meant a nucleic acid molecule which contains the nucleic acid of interest (e.g., the DNA of interest), generally operably linked to a promoter for expression of the polypeptide encoded by the nucleic acid of interest. "Constructs" as used herein is generally meant to refer a nucleic acid molecule that facilitates expression of a polypeptide encoded by the nucleic acid to be introduced into a secretory gland cell.

By "vector" is meant any compound, biological or chemical, that facilitates transformation of a secretory gland cell with a DNA of interest. Exemplary biological vectors include viruses, particularly attenuated and/or replication-deficient viruses. Exemplary chemical vectors include lipid complexes and naked DNA constructs.

By "naked DNA" or "naked nucleic acid" or DNA sequence and the like is meant a nucleic acid molecule that is not contained within a viral particle, bacterial cell or other encapsulating means that facilitates delivery of nucleic acid into the cytoplasm of the target cell. Naked nucleic acid can be associated with means for facilitating delivery of the nucleic acid to the site of the target cell (e.g., means that facilitate travel into the target cell of the nucleic acid through the alimentary canal, protect the nucleic acid from stomach acid, and/or serve to penetrate intestinal mucus) and/or to the surface of the target epithelial cell.

By "promoter" is meant a minimal DNA sequence sufficient to direct transcription. "Promoter" is also meant to encompass those promoter elements sufficient for promoter-dependent gene expression controllable for cell-type specific, tissue-specific or inducible by external signals or agents; such elements may be located in the 5' or 3' regions of the native gene.

By "secretory gland specific promoter" is meant a promoter which directs expression of an operably linked DNA sequence when bound by transcriptional activator proteins, or other regulators of transcription, which are unique to a specific type of secretory gland cell. For example, by "salivary gland specific promoter" is meant a secretory gland specific promoter which directs expression in a salivary gland cell. A salivary amylase promoter is an example of a salivary gland specific promoter. By "pancreas specific promoter" is meant a secretory gland specific promoter which directs expression in a pancreatic cell. Examples of pancreas specific promoters include a pancreatic amylase promoter and an insulin promoter.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that the DNA of interest introduced into the cell is positioned adjacent a DNA sequence which directs transcription and translation of the introduced DNA (i.e., facilitates the production of, e.g., a polypeptide encoded by a DNA of interest).

By "mammalian subject" or "mammalian patient" is meant any mammal to which intravenous protein delivery is desired, including human, bovine, equine, canine, and feline subjects.

By "euglycemia" or "euglycemic state" is meant a state associated with a level of blood glucose that is normal or nearly normal, particularly relative to the levels of blood glucose in a subject having a disease or condition associated with hyperglycemia. In humans, euglycemia correlates with blood glucose levels in the range of 70 mg/dl to 130 mg/dl.

The terms "synergistic," "synergistic effect," and the like are used herein to describe improved effects (e.g, an increase in tissue expression levels in one or more secretory glands, an increased responsiveness to hormonal stimulation to elicit secretion of a polypeptide of interest, or a decrease in an undesirable phenotype) by combining one or more aspects of the invention (e.g., by transformation of more than one secretory gland in a single subject, or by transformation of a secretory gland(s) with multiple constructs encoding the same or different polypeptides).

Overview of the Invention

The present invention features methods for genetically altering a secretory gland cell (i.e., secretory gland cell transformation) and methods of delivering a protein using the methods of genetically altering secretory gland cells. More specifically the invention features methods for delivery of a protein or other product encoded by a nucleic acid sequence of interest to a mammalian subject by expression of a DNA of interest in cells within a secretory gland of a mammalian patient (i.e., by in vivo gene therapy). Preferably, the transformed secretory gland cells expressing the protein encoded by the DNA of interest secrete a therapeutically effective amount of the protein into the bloodstream of the mammalian patient. Preferably, the secretory gland into which the DNA of interest is introduced and expressed is the pancreas, a salivary gland, or the liver. In short, the invention features a delivery system that involves introduction of a nucleic acid sequence encoding a product of interest (e.g., a protein) into a secretory gland cell (e.g., a salivary gland cell, hepatocyte, or pancreatic cell, particularly exocrine cells of salivary gland, liver, or pancreas), expression of the encoded protein, and delivery of the protein into the blood stream by secretion of the protein by the transformed secretory gland cell.

The present invention preferably uses either naked DNA or DNA premixed with adjuvants (e.g., lipofectin or viral particles). It is not necessary to incorporate the DNA into viral particles in order to achieve transformation of secretory gland cells and provide expression of the polypeptide of interest at physiologic/therapeutic levels in the bloodstream.

An important feature of the invention is the use of exocrine cells of glands of the gastrointestinal tract (i.e., pancreas, liver, salivary gland) to produce and secrete therapeutic proteins into blood. While it is well understood that exocrine cells secrete into the lumen of the glands' ducts (i.e. in an exocrine direction), with the exception of the liver (i.e., the hepatocytes secrete cellular products in both directions, e.g. blood proteins into blood and bile satls into the intestinal lumen), it is not widely appreciated that exocrine cells can also secrete significant amounts of protein into the systemic circulation. For example, exocrine proteins such as α-amylase (salivary glands), pepsinogen (gastric glands), various digestive enzymes from the exocrine pancreas, salivary gland kallikreins and nerve growth factor (Liebow, 1988 Pancreas 3:343–351) are normal constituents of blood. In the pancreas, substantial quantities of digestive enzymes are released into the circulation (Saito et al., 1973 Jpn. J. Physiol. 23:477–95; Isenman et al. 1997 Proc. Natl. Acad. Sci (USA) 74:4068–4072; Papp et al. 1980 Acta Physiol. Acad. Sci. Hung. 56:401–410; Geokas et al., 1980 Am. J. Physiol. 238:238–246; Miyasaka et al. 1981 Am. J. Physiol. 241:170–175; Grendell et al. 1982 Am. J. Physiol. 243:54–59). Endocrine secretion can be greatly enhanced by common secretory stimulants (Saito et al., supra; Isenman et al. supra; Miyasaka et al. supra; Grendell et al. supra). As much as 20–25% of the total secreted product can be released into blood as a consequence of stimulation (Grendell et al. supra). The present invention takes advantage of the discovery that exocrine gland cells can be transformed with a desired DNA sequence and secrete the encoded polypeptide into the bloodstream rather than only or primarily into the gastrointestinal tract.

In addition to the advantages described above, the invention also permits access to the cells of secretory glands without invasive procedures. For example, it is possible to cannulate either the collecting duct of a major salivary gland through its orifice in the mouth, or the common bile or pancreatic duct by means of endoscopic retrograde cholangiopancreatography (ERCP). These are common diagnostic procedures performed on awake patients. The non-invasive methods of the invention allow delivery of the DNA of interest in a safe manner that substantially avoids the inflammatory and immunological responses associated with other means of DNA delivery.

The invention also takes advantage of the protein-producing capacity of secretory gland cells. This advantage is particularly useful for the production of hormones such as hGH and insulin, which have short half-lives in blood and are cleared quickly. The cells of the exocrine glands are the body's major protein synthesizing and secreting systems. For example, the human exocrine pancreas manufactures and secretes approximately 20 g of protein daily. According to the present invention, even a small proportion of protein synthesized by secretory glands provides enough secreted product to provide therapeutic protein levels for the treatment of most diseases of circulating proteins.

The invention will now be described in further detail.

Constructs

Any nucleic acid construct having a eukaryotic promoter operably linked to a DNA of interest can be used in the invention. The constructs containing the DNA sequence (or the corresponding RNA sequence) which may be used in accordance with the invention may be any eukaryotic expression construct containing the DNA or the RNA sequence of interest. For example, a plasmid or viral construct (e.g. adenovirus) can be cleaved to provide linear DNA having ligatable termini. These termini are bound to exogenous DNA having complementary, like ligatable termini to provide a biologically functional recombinant DNA molecule having an intact replicon and a desired phenotypic property. Preferably the construct is capable of replication in both eukaryotic and prokaryotic hosts, which constructs are known in the art and are commercially available.

The exogenous (i.e., donor) DNA used in the invention is obtained from suitable cells, and the constructs prepared using techniques well known in the art. Likewise, techniques for obtaining expression of exogenous DNA or RNA sequences in a genetically altered host cell are known in the art (see, for example, Kormal et al., Proc. Natl. Acad. Sci. USA, 84:2150–2154, 1987; Sambrook et al. Molecular Cloning: a Laboratory Manual, 2nd Ed., 1989, Cold Spring Harbor Laboratory Press, Cold Spring Harbor, N.Y.; each of which are hereby incorporated by reference with respect to methods and compositions for eukaryotic expression of a DNA of interest).

Preferably, the DNA construct contains a promoter to facilitate expression of the DNA of interest within a secretory gland cell. Preferably the promoter is a strong, eukaryotic promoter such as a promoter from cytomegalovirus (CMV), mouse mammary tumor virus (MMTV), Rous sarcoma virus (RSV), or adenovirus. More specifically, exemplary promoters include the promoter from the immediate early gene of human CMV (Boshart et al., Cell 41:521–530, 1985) and the promoter from the long terminal repeat (LTR) of RSV (Gorman et al., Proc. Natl. Acad. Sci. USA 79:6777–6781, 1982). Of these two promoters, the CMV promoter is preferred as it provides for higher levels of expression than the RSV promoter.

Alternatively, the promoter used may be a tissue-specific promoter. For example, where the secretory gland is the pancreas, the promoter used in the vector is preferably a pancreas specific promoter, e.g., an insulin promoter or a pancreas α-amylase promoter; where the secretory gland is a salivary gland, the tissue-specific promoter may be a salivary α-amylase promoter or mumps viral gene promoter. Both pancreatic and salivary α-amylase genes have been identified and characterized in both mice and humans (see, for example, Jones et al., *Nucleic Acids Res.*, 17:6613–6623; Pittet et al., *J. Mol. Biol.*, 182:359–365, 1985; Hagenbuchle et al., *J. Mol. Biol.*, 185:285–293, 1985; Schibler et al., *Oxf. Surv. Eukaryot. Genes*, 3:210–234, 1986; and Sierra et al., *Mol. Cell. Biol.*, 6:4067–4076, 1986 for murine pancreatic and salivary α-amylase genes and promoters; Samuelson et al., *Nucleic Acids Res.*, 16:8261–8276, 1988; Groot et al., *Genomics*, 5:29–42, 1989; and Tomita et al., *Gene*, 76:11–18, 1989 for human pancreatic and salivary α-amylase genes and their promoters; Ting et al., *Genes Dev.* 6:1457–65, 1992 for human salivary α-amylase AMY1C promoter sequences).

The constructs of the invention may also include sequences in addition to promoters which enhance secretory gland specific expression. For example, where pancreas specific expression of the DNA of interest is desired, the construct may include a PTF-1 recognition sequence (Cockell et al., *Mol. Cell. Biol.*, 9:2464–2476, 1989). Sequences which enhance salivary gland specific expression are also well known in the art (see, for example, Robins et al., *Genetica* 86:191–201, 1992).

Other components such as a marker (e.g., an antibiotic resistance gene (such as an ampicillin resistance gene) or β-galactosidase) to aid in selection of cells containing and/or expressing the construct, an origin of replication for stable replication of the construct in a bacterial cell preferably, a high copy number origin of replication), a nuclear localization signal, or other elements which facilitate production of the DNA construct, the protein encoded thereby, or both.

For eukaryotic expression, the construct should contain at a minimum a eukaryotic promoter operably linked to a DNA of interest, which is in turn operably linked to a polyadenylation sequence. The polyadenylation signal sequence may be selected from any of a variety of polyadenylation signal sequences known in the art. Preferably, the polyadenylation signal sequence is the SV40 early polyadenylation signal sequence. The construct may also include one or more introns, which can increase levels of expression of the DNA of interest, particularly where the DNA of interest is a cDNA (e.g., contains no introns of the naturally-occurring sequence). Any of a variety of introns known in the art may be used (e.g, the human β-globin intron, which is inserted in the construct at a position 5' to the DNA of interest).

The DNA of interest may be inserted into a construct so that the therapeutic protein is expressed as a fusion protein (e.g., a fusion protein having β-galactosidase or a portion thereof at the N-terminus and the therapeutic protein at the C-terminal portion). Production of a fusion protein can facilitate identification of transformed cells expressing the protein (e.g., by enzyme-linked immunosorbent assay (ELISA) using an antibody which binds to the fusion protein).

The Nucleic Acid (DNA) of Interest

The DNA of interest can be any DNA encoding any protein for which intravenous therapy is desirable. For example, intravenous protein therapy is appropriate in treating a mammalian subject having an inherited or acquired disease associated with a specific protein deficiency (e.g., diabetes, hemophilia, anemia, severe combined immunodeficiency). Such protein deficient states are amenable to treatment by replacement therapy, i.e., expression of a protein to restore the normal bloodstream levels of the protein to at least normal levels.

Alternatively, the DNA of interest may encode a polypeptide that is either normally present in a healthy mammalian subject or which is foreign to the mammalian subject, and which polypeptide is effective in treatment of a condition by expression or over-expression of the polypeptide. For example, the DNA of interest can encode antimicrobial, antiparasitic, antifungal, or antiviral polypeptides for treatment of a mammalian subject having a viral (e.g., human immunodeficiency virus (HIV), Epstein-Barr virus (EBV), herpes simplex virus (HSV), bacterial, fungal, and/or parasitic infection, particularly where the infection is chronic, i.e., persisting over a relatively long period of time. The methods of the invention may also be used to enhance expression of a protein present in a normal mammal, or to express a protein not normally present in a normal mammal, in order to achieve a desired effect (e.g., to enhance a normal metabolic process). For example, a secretory gland of a dairy cow may be transformed with DNA encoding bovine growth hormone (BGH) in order to enhance levels of BGH in the bloodstream and enhance milk production.

The DNA of interest is preferably obtained from a source of the same species as the mammalian subject to be treated (e.g. human to human), but this is not an absolute requirement. DNA obtained from a species different from the mammalian subject can also be used, particularly where the amino acid sequences of the proteins are highly conserved and the xenogeneic protein is not highly immunogenic so as to elicit a significant, undesirable antibody response against the protein in the mammalian host.

Exemplary, preferred DNAs of interest include DNA encoding insulin, growth factors (e.g., growth hormone, insulin-like growth factor-1 (IGF-1), platelet-derived growth factor (PDGF), epidermal growth factor (EGF), acidic fibroblast growth factor, basic fibroblast growth factor, or transforming growth factor β), cytokines (e.g., interferon (INF) (e.g., INF-α2b, INF-α2a, INF-αN1, INF-β1b, INF-γ), interleukin (e.g, IL-2, IL-8), or tumor necrosis factor (TNF) (e.g, TNF--α, TNF-β)), clotting factors (e.g., clotting factor VIII), hormones (e.g, GP-1), antimicrobial polypeptides (e.g., antibacterial, antifungal, antiviral, and/or antiparasitic polypeptides), enzymes (e.g., adenosine deaminase), filgastim (Neupogen), hemoglobin, erythropoietin, insulinotropin, imiglucerase, sarbramostim, antigens, tissue plasminogen activator (tPA), urokinase, streptokinase, endothelian, soluble CD4, and antibodies and/or antigen-binding fragments (e.g, FAbs) thereof (e.g., orthoclone OKT-e (anti-CD3), GPIIb/IIa monoclonal antibody). Preferably, the mammalian subject is a human subject and the DNA expressed encodes a human protein.

Table 1 provides a list of exemplary proteins and protein classes which can be delivered to the bloodstream of a mammalian subject via the method of secretory gland cell transformation of the invention.

TABLE 1

Exemplary Proteins and Protein Classes for Expression in and Secretion by Secretory Gland Cells

SPECIFIC EXEMPLARY PROTEINS

| | |
|---|---|
| insulin | interferon-α2B |
| human growth hormone (hGH) | transforming growth factor (TGF) |
| erythropoietin (EPO) | ciliary neurite transforming factor (CNTF) |
| clotting factor VIII | insulin-like growth factor-1 (IGF-1) |
| bovine growth hormone (BGH) | granulocyte macrophage colony stimulating factor (GM-CSF) |

TABLE 1-continued

Exemplary Proteins and Protein Classes for
Expression in and Secretion by Secretory Gland Cells

| | |
|---|---|
| platelet derived growth factor (PDGF) | interferon-α2A |
| clotting factor VIII | brain-derived neurite factor (BDNF) |
| thrombopoietin (TPO) | insulintropin |
| IL-1 | tissue plasminogen activator (tPA) |
| IL-2 | urokinase |
| IL-1 RA | streptokinase |
| superoxide dismutase (SOD) | adenosine deamidase |
| catalase | calcitonin |
| fibroblast growth factor (FGF) (acidic or basic) | arginase |
| neurite growth factor (NGF) | phenylalanine ammonia lyase |
| granulocyte colony stimulating factor (G-CSF) | γ-interferon |
| L-asparaginase | pepsin |
| uricase | trypsin |
| chymotrypsin | elastase |
| carboxypeptidase | lactase |
| sucrase | intrinsic factor |
| calcitonin | parathyroid hormone(PTH)-like hormone |
| Ob gene product | cholecystokinin (CCK) |
| glucagon | insulinotrophic hormone |
| EXEMPLARY CLASSES OF PROTEINS | |
| enzymes (e.g., proteases, phospholipases, etc.) | pituitary hormones |
| protease inhibitors | growth factors |
| cytokines | somatomedians |
| chemokines | immunoglobulins |
| gonadotrophins | interleukins |
| chemotactins | interferons |
| lipid-binding proteins | |

Numerous proteins that are desirable for intravenous protein therapy are well known in the art and the DNA encoding these proteins has been isolated. For example, the sequence of the DNAs encoding insulin, human growth hormone, intrinsic factor, clotting actor VIII, and erythropoietin are available from Genbank and/or have been described in the scientific literature (e.g., human clotting factor VIII gene: Gitschier et al., *Nature* 312:326–330, 1984; Wood et al., *Nature* 312:330–337, 1984; human intrinsic factor: Hewitt et al., *Genomics* 10:432–440, 1991). Moreover, proteins commonly used in treatments can be used in the procedures of the present invention. Such proteins are disclosed in, for example, the Physicians' Desk Reference (1994 Physicians' Desk Reference, 48th Ed., Medical Economics Data Production Co., Montvale, N.J.; incorporated by reference) and can be dosed using methods described in Harrison's Principles of Internal Medicine and/or the AMA "Drug Evaluations Annual" 1993, all incorporated by reference.

Where the DNA encoding a protein of interest has not been isolated, this can be accomplished by various, standard protocols well known to those of skill in the art (see, for example, Sambrook et al., ibid; Suggs et al., *Proc. Natl. Acad. Sci. USA* 78:6613–6617, 1981; U.S. Pat. No. 4,394,443; each of which are incorporated herein by reference with respect to identification and isolation of DNA encoding a protein of interest). For example, genomic or cDNA clones encoding a specific protein can be isolated from genomic or cDNA libraries using hybridization probes designed on the basis of the nucleotide or amino acid sequences for the desired gene. The probes can be constructed by chemical synthesis or by polymerase chain reaction (PCR) using primers based upon sequence data to amplify DNA fragments from pools or libraries (U.S. Pat. Nos. 4,683,195 and 4,683,202). Nucleotide substitutions, deletions, additions, and the like can also be incorporated into the polynucleotides, so long as the ability of the polynucleotide to hybridize is not substantially disrupted. (Sambrook et al. ibid). The clones may be expressed or the DNA of interest can be excised or synthesized for use in other constructs. If desired, the DNA of interest can be sequenced using methods well known in the art.

It may also be desirable to produce altered forms of the therapeutic proteins that are, for example, protease resistant or have enhanced activity relative to the wild-type protein. For example, where the therapeutic protein is a hormone, it may be desirable to alter the protein's ability to form dimers or multimeric complexes. For example, insulin may be modified so as to prevent its dimerization has a more rapid onset of action relative to wild-type, dimerized insulin.

Vectors for Delivery of the DNA of Interest to the Secretory Gland Cell

The vectors for delivery of the DNA of interest can be either viral or non-viral, or may be composed of naked DNA admixed with an adjuvant such as viral particles (e.g, adenovirus) or cationic lipids or liposomes. An "adjuvant" is a substance that does not by itself produce the desired effect, but acts to enhance or otherwise improve the action of the active compound. The precise vector and vector formulation used will depend upon several factors such as the secretory gland targeted for gene transfer.

Non-viral vectors

The DNA of interest may be administered using a non-viral vector. "Non-viral vector" as used herein is meant to include naked DNA, chemical formulations containing naked DNA (e.g, a formulation of DNA and cationic compounds (e.g., dextran sulfate)), and naked DNA mixed with an adjuvant such as a viral particle (i.e., the DNA of interest is not contained within the viral particle, but the transforming formulation is composed of both naked DNA and viral particles (e.g., adenovirus particles) (see, e.g., Curiel et al. 1992 Am. J. Respir. Cell Mol. Biol. 6:247–52). Thus "non-viral vector" can include vectors composed of DNA plus viral particles where the viral particles do not contain the DNA of interest within the viral genome.

In one preferred embodiment, the formulation comprises viral particles which are mixed with the naked DNA construct prior to administration. Preferably, about $10^8$ to $10^{10}$ viral particles (preferably about $1\times10^{10}$ to $5\times10^{10}$, more preferably about $3\times10^{10}$ particles) are mixed with the naked DNA construct (about 5 μg to 50 μg DNA, more preferably about 8 μg to 25 μg DNA) in a total volume of about 100 μl. Preferably the viral particles are adenovirus particles (Curiel et al., 1992 supra).

Alternatively or in addition, the DNA of interest can be complexed with polycationic substances such as poly-L-lysine or DEAC-dextran, targeting ligands, and/or DNA binding proteins (e.g, histones). DNA- or RNA-liposome complex formulations comprise a mixture of lipids which bind to genetic material (DNA or RNA) and facilitate delivery of the nucleic acid into the cell. Liposomes which can be used in accordance with the invention include DOPE (dioleyl phosphatidyl ethanol amine), CUDMEDA (N-(5-cholestrum-3-β-ol 3-urethanyl)-N',N'-dimethylethylene diamine).

For example, the naked DNA can be administered in a solution containing Lipofectin™ LTI/BRL) at a concentrations ranging from about 2.5% to 15% volume: volume, preferably about 6% to 12% volume:volume. Preferred methods and compositions for formulation of DNA for delivery according to the method of the invention are described in U.S. Pat. No. 5,527,928, incorporated herein by reference.

The DNA of interest can also be administered as a chemical formulation of DNA or RNA coupled to a carrier molecule (e.g., an antibody or a receptor ligand) which facilitates delivery to host cells for the purpose of altering the biological properties of the host cells. By the term "chemical formulations" is meant modifications of nucleic acids to allow coupling of the nucleic acid compounds to a carrier molecule such as a protein or lipid, or derivative thereof. Exemplary protein carrier molecules include antibodies specific to the cells of a targeted secretory gland or receptor ligands, i.e., molecules capable of interacting with receptors associated with a cell of a targeted secretory gland.

Viral vectors

In general, viral vectors used in accordance with the invention are composed of a viral particle derived from a naturally-occurring virus which has been genetically altered to render the virus replication-defective and to express a recombinant gene of interest in accordance with the invention. Once the virus delivers its genetic material to a cell, it does not generate additional infectious virus but does introduce exogenous recombinant genes into the cell, preferably into the genome of the cell.

Numerous viral vectors are well known in the art, including, for example, retrovirus, adenovirus, adeno-associated virus, herpes simplex virus (HSV), cytomegalovirus (CMV), vaccinia and poliovirus vectors. Retroviral vectors are less preferred since retroviruses require replicating cells and secretory glands are composed of mostly slowly replicating and/or terminally differentiated cells. Adenovirus is a preferred viral vector since this virus efficiently infects slowly replicating and/or terminally differentiated cells. The viral vector may be selected according to its preferential infection of the targeted secretory gland (e.g., where the secretory gland is a salivary gland, the viral vector may be derived from an attenuated (i.e., does not cause significant pathology or morbidity in the infected host, e.g, the virus is nonpathogenic or causes only minor disease symptoms) and/or replication-deficient mumps virus or other attenuated and/or replication-deficient virus which is substantially specific for salivary gland cells).

Where a replication-deficient virus is used as the viral vector, the production of infective virus particles containing either DNA or RNA corresponding to the DNA of interest can be produced by introducing the viral construct into a recombinant cell line which provides the missing components essential for viral replication. Preferably, transformation of the recombinant cell line with the recombinant viral vector will not result in production of replication-competent viruses, e.g., by homologous recombination of the viral sequences of the recombinant cell line into the introduced viral vector. Methods for production of replication-deficient viral particles containing a nucleic acid of interest are well known in the art and are described in, for example, Rosenfeld et al., Science 252:431–434, 1991 and Rosenfeld et al., Cell 68:143–155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus). Methods and materials for manipulation of the mumps virus genome, characterization of mumps virus genes responsible for viral fusion and viral replication, and the structure and sequence of the mumps viral genome are described in Tanabayashi et al., J. Virol. 67:2928–2931, 1993; Takeuchi et al., Archiv. Virol., 128:177–183, 1993; Tanabayashi et al., Virol. 187:801–804, 1992; Kawano et al., Virol., 179:857–861, 1990; Elango et al., J. Gen. Virol. 69:2893–28900, 1988.

Conditions or Diseases Amenable to Treatment Using the Method of the Invention

Various disease conditions are amenable to treatment using the methods of the invention. One skilled in the art can recognize the appropriate protein which should be produced by the invention for treating specific disease conditions. Exemplary diseases which are amenable to treatment using the subject invention, and exemplary, appropriate proteins which can be used in treating these diseases, are shown in Table 2.

TABLE 2

Exemplary Disease Conditions Amenable to Treatment Using the Invention

| Enzyme Deficiency | Endotoxic Shock/Sepsis |
|---|---|
| Adenosine deaminase[1] | Lipid-binding protein (LBP) |
| Purine nucleotide phosphorylase | |
| Galactosidase | |
| β-glucuronidase | |
| Antioxidants for Cancer Therapy | Anemia |
| Superoxide dismutase | Erythropoietin |
| Catalase | |
| Cancer | Growth Factors (for use in wound healing, induction of red blood cell formation, etc.) |
| α-Interferon | |
| γ-Interferon | |
| α-IL1 | Epidermal growth factor |
| Phenylalanine ammonia lyase | G-CSF |
| Arginase | γ-Interferon |
| L-asparaginase | Transforming growth factor |
| Uricase | Erythropoietin |
| Granulocyte colony stimulating factor (G-CSF) | Thrombopoietin |
| | Insulin-like growth factor-1 |
| Monoclonal antibodies | Insulin |
| Tissue necrosis factor | Human growth hormone |
| Cardiovascular Disease | Diabetes |
| Tissue plasminogen activator | Insulin |
| Urokinase (native or chimeric) | Glucagon |
| $\alpha_1$-antitrypsin | Insulinotrophic hormone |
| Antithrombin-III | Clotting disorders |
| Other proteases or protease inhibitors | Clotting factor VIII |
| Apolipoproteins (particularly B-48) | |
| Circulating Scavenger Receptor APO A1[2] | |
| Obesity and Feeding | Gastrointestinal and Pancreatic Deficiencies |
| Ob gene product | |
| Cholecystokinin (CCK) | Pepsin (for esophageal reflux) Trypsin |
| Bone diseases | Chymotrypsin |
| Calcitonin | Elastase |
| PTH-like hormone | Carboxypeptidase |
| | Lactase (for lactose deficiency) |
| | Sucrase; Intrinsic Factor (pernicious anemia) |
| Organ-Specific Autoimmune diseases (target of antibody in parentheses) | |
| Myasthenia gravis (acetylcholine receptors) | |
| Graves' disease (thyroid-stimulating hormone receptor) | |
| Thyroiditis (thyroid, peroxidase) | |
| Insulin-resistant diabetes with acanthosis nigricans or with ataxia telangiectasia (Insulin receptor) | |
| Allergic rhinitis, asthma (Beta$_2$-adrenergic receptors) | |
| Juvenile insulin-dependent diabetes (insulin, GAD65) | |

TABLE 2-continued

Exemplary Disease Conditions Amenable to
Treatment Using the Invention

Pernicious anemia (gastric parietal cells, vitamin $B_{12}$ binding site of intrinsic factor)
Addison's disease (adrenal cells)
Idiopathic hypoparathyroidism (parathyroid cells)
Spontaneous infertility (sperm)
Premature ovarian failure (interstitial cells, corpus luteum cells)
Pemphigus (intercellular substance of skin and mucosa)
Bullous pemphigoid (basement membrane zone of skin and mucosa)
Primary biliary cirrhosis (mitochondria)
Autoimmune hemolytic anemia (erythrocytes)
Idiopathic thrombocytopenic purpura (platelet)
Idiopathic neutropenia (neutrophils)
Vitiligo (melanocytes)
Osteosclerosis and Meniere's disease (type II collagen)
Chronic active hepatitis (nuclei of hepatocytes)
Systemic Autoimmune Diseases (defect/organ affected in parentheses)

Goodpasture's syndrome (basement membranes)
Rheumatoid arthritis (γ-globulin, EBV-related antigens, collagen types II and III)
Sjögren's syndrome (γ-globulin, SS-A (Ro), SS-B (La))
Systemic lupus erythematosus (nuclei, double-stranded DNA, single-stranded DNA, Sm ribonucleoprotein, lymphocytes, erythrocytes, neurons, γ-globulin)
Scleroderm (nuclei, Scl-70, SS-A(Ro), SS-B (La), centromere)
Polymyositis (nuclei, Jo-1, PL-7, histadyl-tRNA or threonyl-tRNA synthetases, PM-1, Mi-2)
Rheumatic fever (myocardium heart valves, choroid plexus)

[1]For treatment of severe combined immunodeficiency
[2]Converts low-density lipoproteins to high-density lipoproteins

Transformation of Secretory Gland Cells

The DNA of interest-containing vector (i.e., either a viral or non-viral vector (including naked DNA)) is introduced into the secretory gland in vivo via the duct system (i.e., by retrograde ductal injection, which may be accomplished by perfusion (i.e., continuous injection), or by a single, discontinuous injection). Retrograde ductal injection may be accomplished in the pancreas and liver by endoscopic retrograde chalangio-pancreatography (ECRP). Ductal administration provides several advantages. Because the vector is presented to the cells from "outside" the body (from the lumen), the immunological and inflammatory reactions that are commonly observed as a result of the administration of transforming formulations and their adjuvants into blood and interstitial fluid may be avoided.

Moreover, the cells of secretory glands form a monolayer that encloses the duct system. As a consequence, virtually all of the cells of the glands can be accessed by a single administration into the duct. In this way it is possible to transfect large masses of cells in a relatively simple manner with a single procedure. The DNA of interest can thus also be administered without substantial dilution (it is only diluted by the fluid in the duct system) and without the need to develop organ specific targeting signals. In contrast, intravenous administration necessarily greatly dilutes the material and requires that it be targeted to the organ of interest in some fashion.

The amount of DNA to transform a sufficient number of secretory gland cells and provide for expression of therapeutic levels of the protein can be readily determined using an animal model (e.g., a rodent (mouse or rat) or other mammalian animal model) to assess factors such as the efficiency of transformation, the levels of protein expression achieved, the susceptibility of the targeted secretory gland cells to transformation, and the amounts of DNA required to transform secretory gland cells.

The precise amount of DNA administered will vary greatly according to a number of factors including the susceptibility of the target cells to transformation, the size and weight of the subject, the levels of protein expression desired, and the condition to be treated. For example, the amount of DNA introduced into a secretory gland of a human is generally from about 1 μg to 200 mg, preferably from about 100 μg to 100 mg, more preferably from about 500 μg to 50 mg, most preferably about 10 mg. Specifically, the amount of DNA introduced into the pancreas of a human is, for example, generally from about 1 μg to 100 mg, preferably about 100 μg to 10 mg, more preferably from about 250 μg to 5 mg, still more preferably from about 500 μg to 1.5 mg, most preferably about 1 mg. The amount of DNA introduced into the salivary gland of a human is, for example, generally from about 2.5 μg to 30 mg, more preferably from about 25 μg to 3 mg, still more preferably from about 100 μg to 1 mg, most preferably about 250 μg. The amount of DNA introduced into the liver of a human is, for examples, generally from about 10 μg to 500 mg, more preferably from about 100 μg to 300 mg, still more preferably from about 150 μg to 100 mg, most preferably about 1 mg.

Generally, the amounts of DNA for human therapy according to the invention can be extrapolated from the amounts of DNA effective for therapy in an animal model. For example, the amount of DNA for therapy in a human is roughly 100 times the amount of DNA effective in therapy in a rat. The amount of DNA necessary to accomplish secretory gland cell transformation will decrease with an increase in the efficiency of the transformation method used.

Concurrent Transformation of Multiple Secretory Glands

In a preferred embodiment of the invention, at least two secretory glands are transformed according to the methods of the invention. Any two secretory glands can be transformed concurrently. For example, the DNA of interest can be administered to both the pancreas and the liver, or to both the salivary gland and the pancreas, or to both the salivary gland and the liver, or to all three. Preferably, cells of the pancreas and the liver are concurrently transformed.

Concurrent transformation of the secretory glands can be carried out several hours to several days apart or, preferably, simultaneously (i.e., DNA is introduced into the two secretory glands during the same procedure. For example, where the liver and pancreas are to be concurrently transformed, the DNA formulation can be introduced simultaneously via a common duct, or separately (e.g., first via the pancreatic duct with occlusion of the hepatic duct, then vice versa).

Concurrent transformation of at least two or more secretory glands can advantageously provide higher levels of expression of the polypeptide of interest in a secretory gland tissue and/or in the bloodstream and can, unexpectedly, provide for synergy between the organs (e.g., to provide for higher levels of tissue expression in a secretory gland than when the secretory gland is transformed alone). For example, concurrent transformation of the pancreas and the liver results in increased levels of tissue expression in the pancreas relative to tissue levels in pancreas when it is transformed alone.

Moreover, the liver releases the polypeptide of interest in a continuous fashion that is not regulated by hormonal stimulation. The pancreas provides a relatively lower level of constitutive secretion and stores most of the polypeptide of interest and only releases large amounts after stimulation (e.g., after the individual eats). Therefore, transformation of both liver and pancreas has the advantage of providing both constitutive secretion primarily form the liver, and hormonally-regulated secretion from the pancreas.

Intravenous protein therapy by transformation of salivary gland, pancreatic, and liver cells Secretory glands transformed according to the invention facilitate high levels expression of a DNA of interest, particularly where the DNA of interest is operably linked to a strong eukaryotic promoter (e.g., CMV, MMTV). The expressed protein is then secreted at high levels into the bloodstream. The protein so expressed and secreted is thus useful in treating a mammalian subject having a variety of conditions.

In a preferred embodiment, the proteins are secreted into the bloodstream at levels sufficient for intravenous protein therapy. For example, the amount of a specific protein normally released into the blood from the pancreas can be substantial, e.g., a specific protein that is released into the bloodstream can be as much as 25% of the amount of duct-directed secretion of that specific protein. This amounts to as much as 1–2 mg of protein/gram of tissue being directed into the blood per hour.

Bloodstream levels of the therapeutic protein may be enhanced by several different methods. For example, bloodstream levels can be enhanced by increasing the overall level of expression of the desired protein, e.g., by integration of multiple copies of the DNA of interest into the genome of the target cells, by operably linking a strong promoter (e.g., a promoter from CMV) and/or enhancer elements to the DNA of interest in the construct, or by transformation of a greater number of target cells in the subject (e.g., by administration of multiple doses of the transforming material).

Secretion of the therapeutic protein into the bloodstream can also be enhanced by incorporating leader sequences, amino acid sequence motifs, or other elements that mediate intravenous-directed secretion into the sequence of the therapeutic protein. For example, the DNA of interest can be engineered to contain a secretion signal that directs secretion of the protein primarily into the bloodstream, thereby increasing the amount of the protein produced in the secretory gland that reaches in the bloodstream. Intravenous-directed secretion signals can be identified by, for example, site-directed mutagenesis of DNA encoding a bloodstream-targeted protein (e.g., insulin). The mutants can be screened by expression of the mutated DNA in secretory gland cells and subsequently determining the ratio of, for example, salivary to intravenous expression.

Alternatively, intravenous-directed secretion signals can be identified by constructing recombinant, chimeric proteins composed of, for example, a putative intravenous secretion signal inserted into a saliva-directed protein. Intravenous secretion signals would then be identified by their ability to re-direct expression of the saliva-directed protein into the bloodstream. Putative intravenous secretion signals and duct system secretion signals can also be identified by comparison of DNA and amino acid sequences of proteins which are preferentially secreted into the bloodstream. Areas of homology or common motifs among the proteins could then be tested as described above.

Overall secretion from secretory glands can be augmented by hormonal stimulation. For example, where the protein is primarily secreted into the duct system and is secreted at lower levels into the bloodstream, hormonal stimulation enhances intravenous secretion as well as secretion into the duct. Thus, therapeutically effective levels of the protein the bloodstream may be achieved or enhanced by administration of an appropriate, secretory gland specific hormone. For example, secretory gland secretion can be enhanced by administration of a cholinergic agonist such as acetyl-β-methyl choline, or can be augmented or further augmented by control of diet (i.e., eating stimulates pancreatic and salivary gland secretion). Thus, because eating a meal can elicit a secretory response, adjustment of meals (e.g., frequency of meals and/or amounts eaten) can be used as a dosing mechanism for delivery of the desired protein, and can be accomplished without administration of additional protein-encoding DNA.

Bloodstream-directed secretion can also be regulated at either the level of transcription, translation, or secretion. Transcriptional regulation involves the timing and level of transcription directed from the DNA of interest, while translational regulation involves the production of polypeptides from transcribed RNA. Secretory regulation involves the release of polypeptides from the cell (e.g., from secretory cells in which the polypeptides to be secreted are stored within intracellular vacuoles). Methods for providing transcriptional and/or translational regulation of a DNA of interest are well known in the art (e.g, transcriptional regulation through the use of inducible promoters).

Secretory regulation can be achieved by, for example, administration of a hormone that elicits a secretory response in the desired secretory gland, or by activity that stimulates production of such hormone(s) (e.g., eating to stimulate pancreatic secretion). Unlike regulation at the level of transcription or translation, which can take many hours to become effective, regulation of secretion occurs within minutes after stimulation. Moreover, endocrine secretion from the pancreas and salivary glands is stimulated by hormones and neurotransmitters that are natural components of the feeding response; thus feeding itself can act as a dosing mechanism.

The actual number of transformed secretory gland cells required to achieve therapeutic levels of the protein of interest will vary according to several factors including the protein to be expressed, the level of expression of the protein by the transformed cells, the rate of protein secretion, the partitioning of the therapeutic protein between the gastrointestinal tract and the bloodstream, and the condition to be treated. For example, the desired intravenous level of therapeutic protein can be readily calculated by determining the level of the protein present in a normal subject (for treatment of a protein deficiency), or by determining the level of protein required to effect the desired therapeutic result.

Application of the Method of the Invention to Achieve Euglycemia in a Diabetic Syndrome In another preferred embodiment of the invention, pancreatic cells are transformed using insulin-encoding DNA to provide for expression and secretion of insulin into the bloodstream of a mammalian subject. Transformation of pancreatic cells with insulin encoding DNA not only provides for regulated expression of insulin in a mammalian subject, but also provides for maintenance of a euglycemic state (i.e., normal blood glucose levels) in diabetic subjects for extended periods of time (e.g., up to 6 to 7 days post transformation). Thus, not only is the exocrine pancreas secreting insulin to reduce blood sugar, but regulating its secretion so that blood levels are maintained at normal levels, e.g, are regulated. Thus, pancreatic transformation with insulin-encoding DNA can be used in the therapy of individuals having a disease or condition associated with elevated blood glucose levels (e.g., diabetes (e.g., type I or type II diabetes), and hyperglycemia). This aspect of the invention may be applied to regulate levels of other proteins in the bloodstream.

Assessment of Protein Therapy

The effects of expression of the protein encoded by the DNA of interest following in vivo transfer of the DNA of interest can be monitored in a variety of ways. Generally, a sample of blood from the subject can be assayed for the presence of the therapeutic protein. Appropriate assays for detecting a protein of interest in blood samples are well known in the art. For example, a sample of blood can be tested for the presence of the polypeptide using an antibody which specifically binds the polypeptide in an ELISA assay. This assay can be performed either qualitatively or quantitatively. The ELISA assay, as well as other immunological assays for detecting a polypeptide in a sample, are described in *Antibodies: A Laboratory Manual* (1988, Harlow and Lane, eds. Cold Spring Harbor Laboratory, Cold Spring Harbor, N.Y.).

Alternatively, or in addition, the efficacy of the polypeptide therapy can be assessed by testing a sample of blood for an activity associated with the polypeptide (e.g., an enzymatic activity). Furthermore, the efficacy of the therapy using the methods of the invention can be assessed by monitoring the condition of the mammalian subject for improvement. For example, where the polypeptide is erythropoietin, the subject's blood is examined for iron content or other parameters associated with anemia.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

EXAMPLE 1

Figure 2:
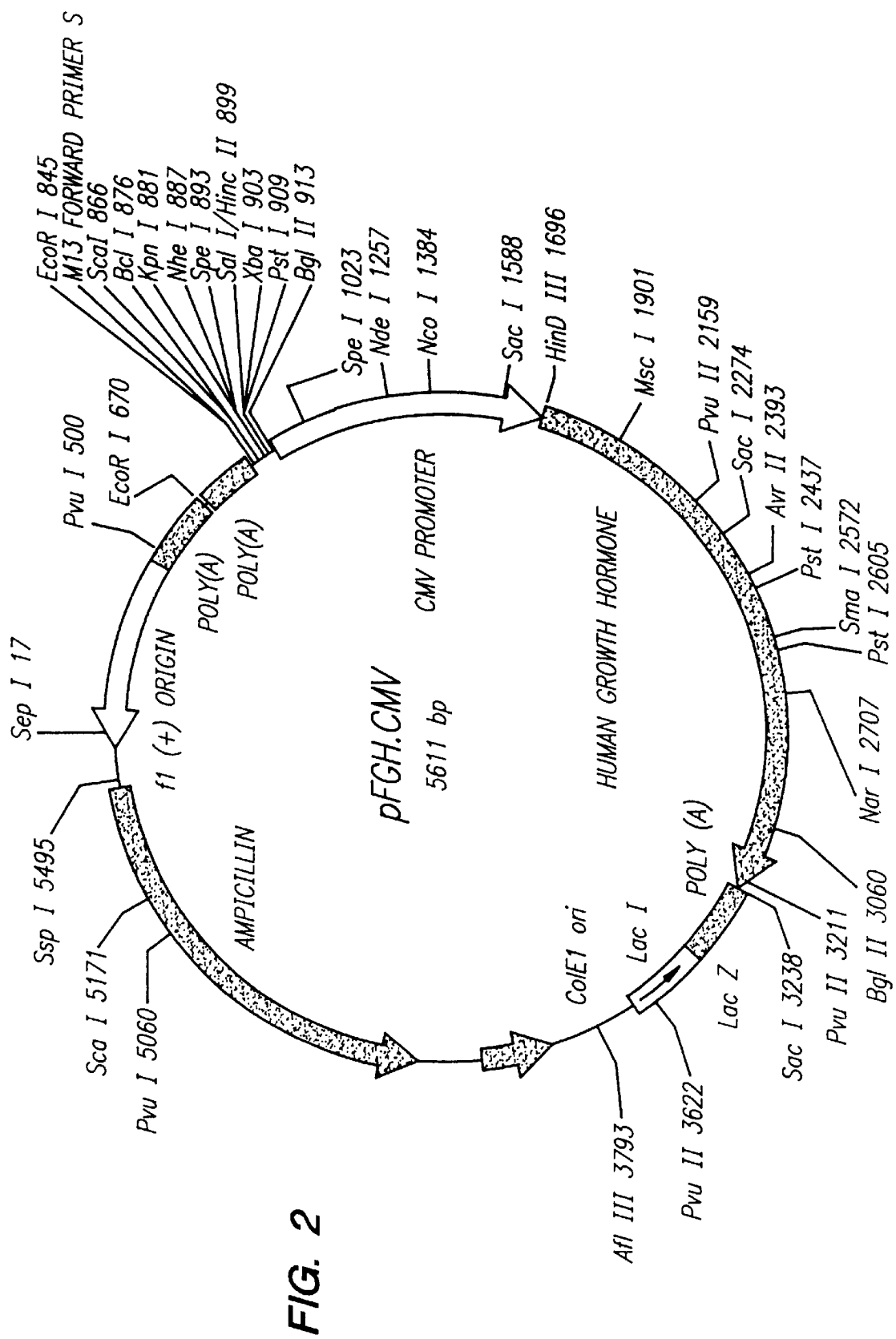
FIG. 2 is a map of the pFGH.CMV construct, which contains the hGH genomic sequence operably linked to the CMV promoter.
Figure 3:
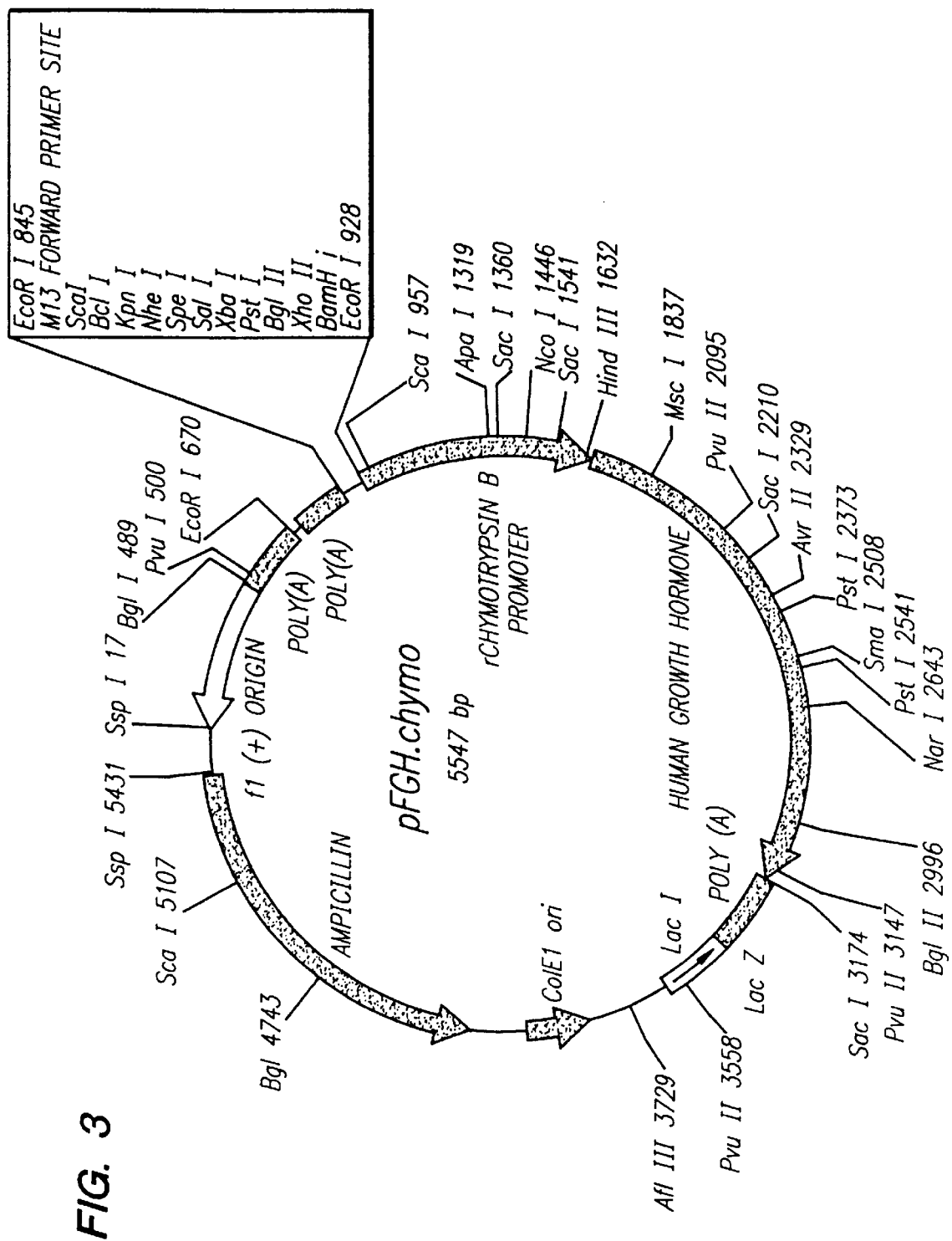
FIG. 3 is a map of the pFGH.chymo construct, which contains the hGH genomic sequence operably linked to the chymotrypsin B promoter.

In vivo gene transfer of DNA encoding human growth hormone by retrograde injection of DNA into the pancreas Four constructs for expression of human growth hormone (hGH) were prepared using techniques well known in the art (see, for example, Sambrook et al. ibid). The first construct, pFGH, contains the genomic hGH DNA sequence inserted in the commercially available vector pBLUESCRIPT SK+™ (Stratagene, LaJolla Calif.) (FIG. 1). Because the hGH coding sequence is not linked to a promoter, this vector provides for no or only low-level hGH expression. Thus, the pFGH construct serves as a negative control for hGH expression in the pancreas. The second construct, pFGH.CMV, was constructed by operably inserting the promoter from the immediate early gene of human CMV upstream of the genomic hGH sequence of the pFGH vector (FIG. 2). The third construct, pFGH.chymo, was constructed by operably inserting the rat chymotrypsin B gene promoter upstream of the genomic hGH sequence of the pFGH vector (FIG. 3). The fourth construct, pFGH.RSV, was constructed by operably inserting the promoter from the long terminal repeat (LTR) of RSV upstream of the genomic hGH sequence of the pFGH vector.

Each of the four vectors was used to transfect the pancreas of approximately 300 g adult male, Sprague-Dawley rats (pFGH+lipofectin, 4 rats; pFGH.chymo+lipofectin, 4 rats; pFGH.RSV+lipofectin, 4 rats; pFGH.CMV+lipofectin, 10 rats; pFGH.CMV without lipofectin, 7 rats; negative control (no DNA, no lipofectin), 3 rats). Pancreatic transfection was accomplished by first anesthetizing the rats and performing a laparotomy to expose the duodenum. The pancreas and the associated common bile duct were identified, and the common bile duct was cannulated either extraduodenally or through the papilla of Vater. The hepatic duct was occluded, and 100 μl of phosphate-buffered saline (PBS) containing one of the four vectors, or 100 μl of PBS alone as a negative control, were slowly injected or infused into the pancreatic duct in a retrograde direction. The vector-containing solutions were composed of 8 μg DNA per 100 μl in PBS, either with or without 6% lipofectin, a cationic lipid used to increase transfection efficiency. The solution was left in place for 5 min before secretory flow was allowed to resume and hepatic duct blockage removed. The catheter was left in place and inserted into the duodenum through a small hole to ensure adequate biliary and pancreatic flow post-operatively. The abdomen was then closed with sutures. The animals recovered fully and rapidly from the surgery without obvious side effects. This transfection method provides direct access of the vector to over 90% of the pancreatic gland cells.

At 48 hr after surgery, a blood sample was obtained to measure serum hGH levels, and the rats were sacrificed. At autopsy, the pancreas of both control and test rats appeared normal, and exhibited no gross or microscopic pathology.

The pancreas was dissected free from the mesenteric surface and was homogenized in cold 0.2 M (pH 8.0) sodium phosphate buffer (1:10 w/v) containing protease inhibitors aprotinin, leupeptin, pepstatin, and PEFABLOC SC™. Homogenization was completed by shearing after 10 passes with a motorized pestle at approximately 4000 rpm in a glass homogenizer. The homogenate was then centrifuged at 1000 g for 15 min. The supernatant was collected and stored at −80° C. until analysis. The levels of hGH in the serum and pancreatic protein samples were measured using the hGH radioimmune assay (Nichols Institute). Each assay was performed in duplicate and compared to a set of control samples.

Figure 4:
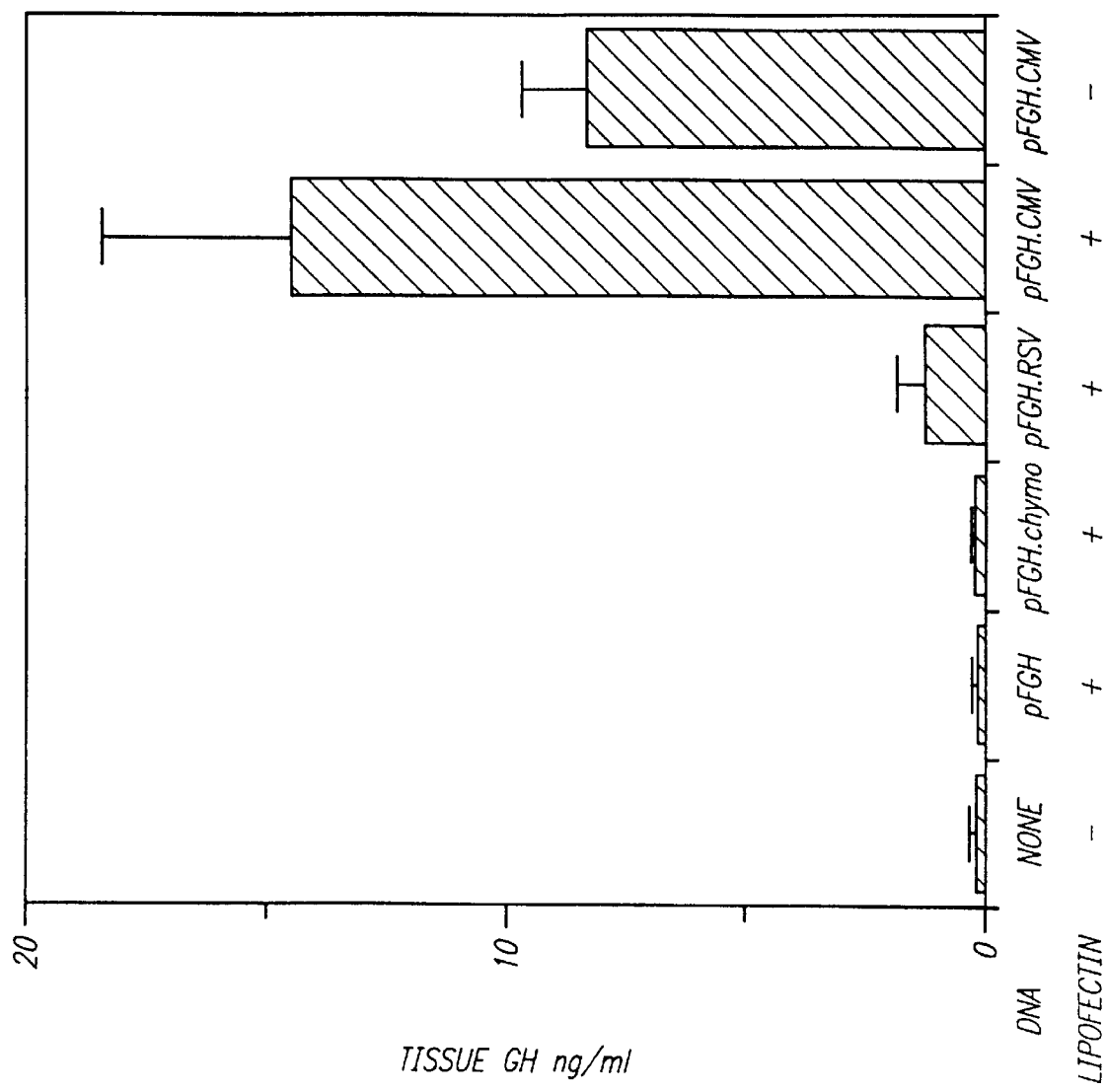
FIG. 4 is a graph showing the levels of tissue expression of hGH expression in the pancreas of rats after retrograde injection with either a control containing no DNA or a test sample containing a hGH construct.
Figure 5:
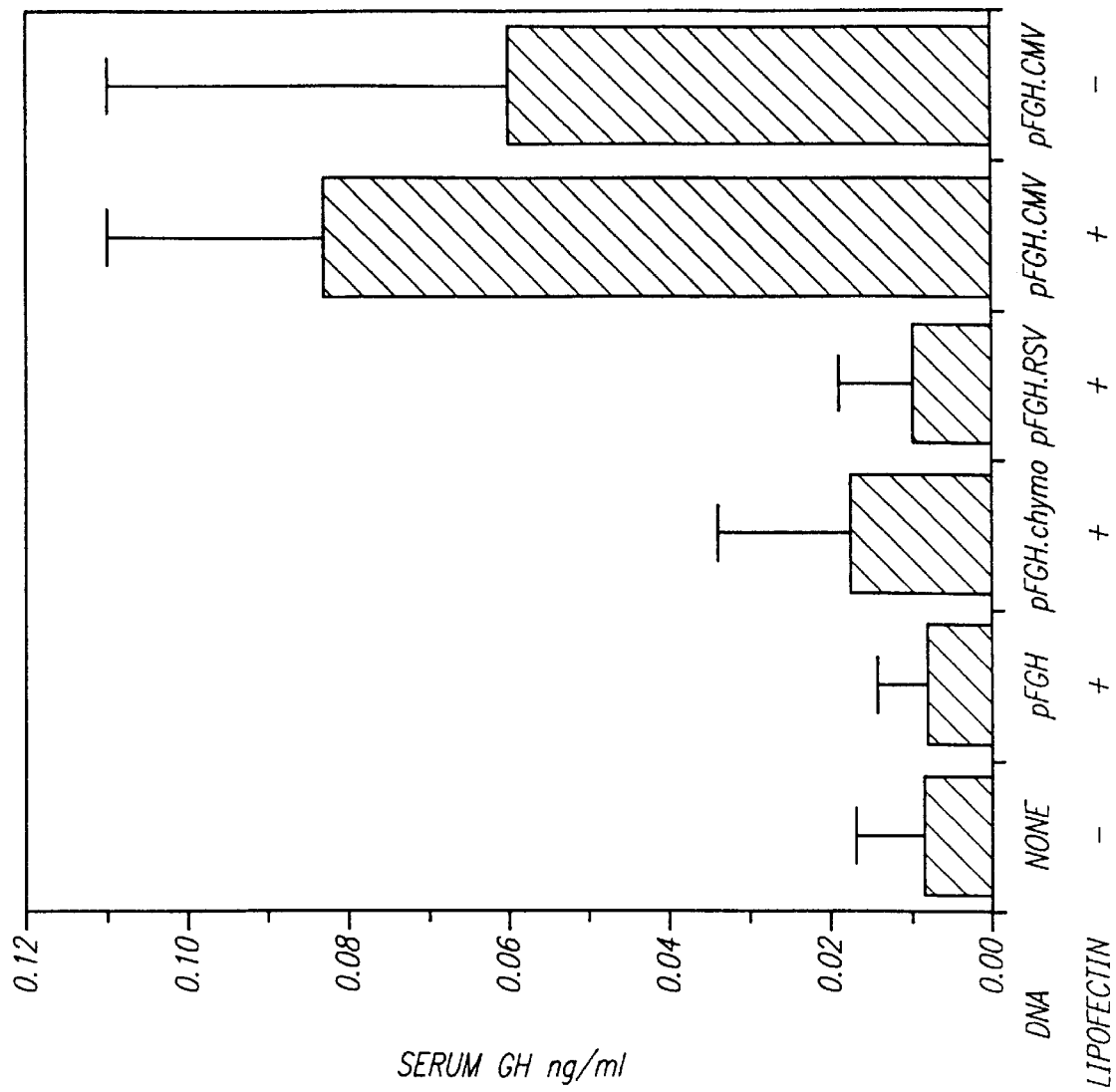
FIG. 5 is a graph showing the serum levels of hGH in rats after retrograde pancreatic injection with either a control containing no DNA or a test sample containing a human growth hormone construct.
Figure 6:
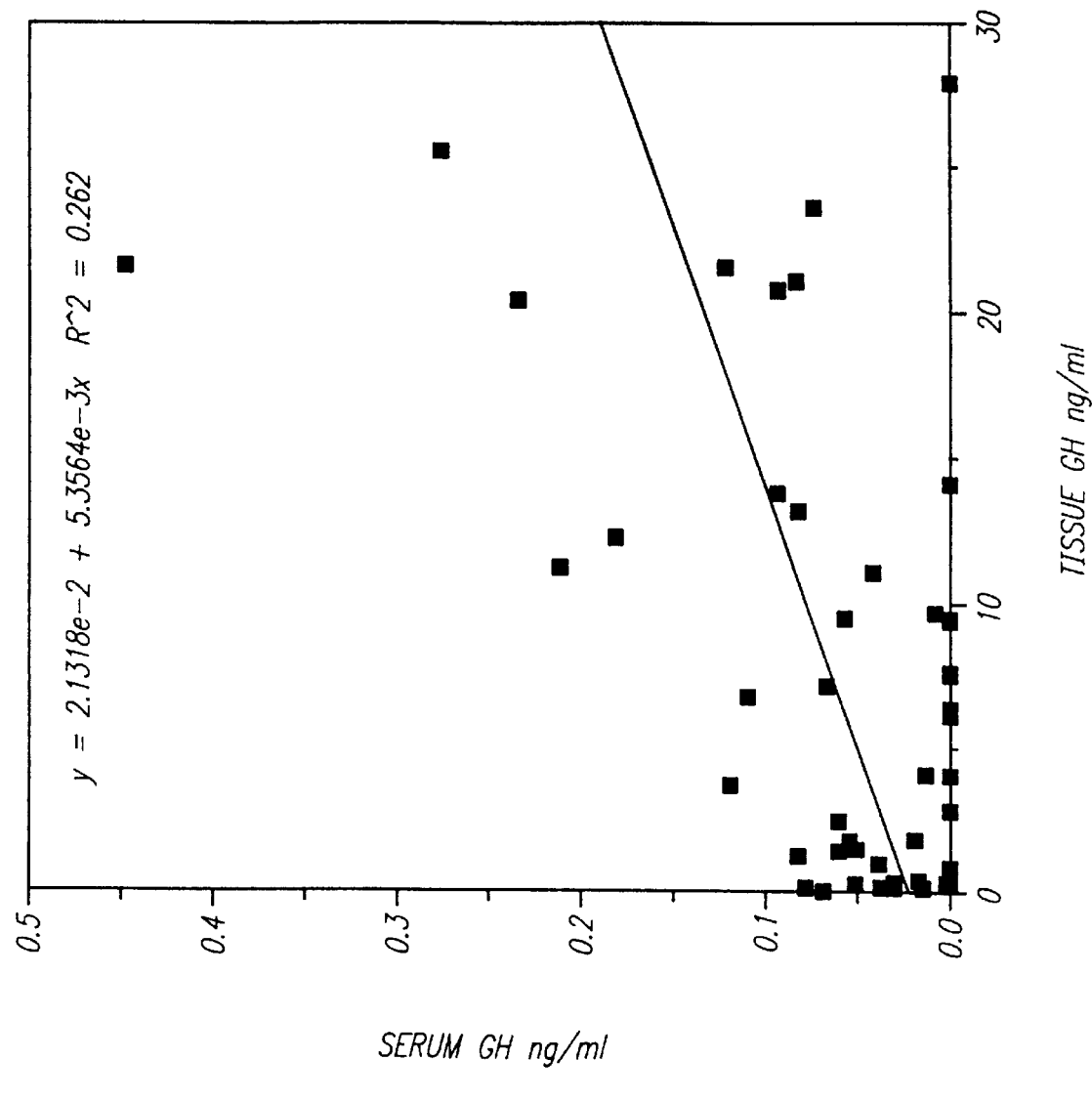
FIG. 6 is a graph showing the correlation between pancreatic tissue expression and serum levels of hGH.

Rats injected with the pFGH.CMV vector expressed higher levels of hGH in the pancreatic tissue (FIG. 4), compared to background levels of pancreatic hGH expression in rats injected with either no DNA (PBS alone) or the pFGH vector (hGH DNA with no promoter). The addition of lipofectin modestly increased hGH expression in rats injected with the pFGH.CMV construct. In addition, rats transfected with the pFGH.CMV vector secreted hGH in the serum at levels increased relative to background levels and to hGH secretion levels in rats injected with either control samples (no DNA or pFGH) or with samples containing hGH DNA linked to either the chymotrypsin B or RSV promoters (FIG. 5). In FIG. 6, all data from the above experiments (including all controls and vectors) are analyzed by plotting the hGH serum levels against the hGH tissue levels. This graph shows that higher tissue levels result in higher levels of secretion into the blood. Thus, retrograde pancreatic injection of the pFGH.CMV vector successfully transfected pancreatic cells to provide both hGH pancreatic tissue expression and hGH secretion into the bloodstream.

EXAMPLE 2

In Vivo Transformation of Pancreatic Cells by Retrograde Ductal Injection of hGH-Encoding DNA and Regulation of hGH Secretion Eight rats were anesthetized and control blood samples (no DNA) were collected from the femoral vein of each animal. Pancreatic transfection was accomplished by exposing the duodenum by laparotomy and identifying the pancreas and the associated common bile duct. The common bile duct was cannulated either extraduodenally or through the papilla of Vater, and the hepatic duct was occluded. A 1:50 dilution of replication-defective human adenovirus (Ad5-di 342) supernatant in 100 µl of phosphate-buffered saline (PBS) containing 8 µg of the hGH-encoding plasmid pFGH.CMV (FIG. 2) was slowly infused into the pancreatic duct in a retrograde direction. The solution was left in place for approximately 5 min before secretory flow was allowed to resume and the hepatic duct blockage removed. The catheter was left in place and inserted into the duodenum through a small hole to ensure adequate biliary and pancreatic flow post-operatively. The abdomen was then closed with sutures. The animals recovered fully and rapidly from the surgery without obvious side effects.

At 48 hr after surgery, a blood sample was obtained to measure serum hGH levels (unstimulated serum levels). The cholinergic agonist McH was injected subcutaneously into each rat at 0.8 mg/kg body weight. Blood samples were collected from the inferior vena cava of each animal at 15 min intervals following McH injection. Serum was separated from the blood of all samples after clotting, and kept at −20° C. prior to assay.

Figure 9:
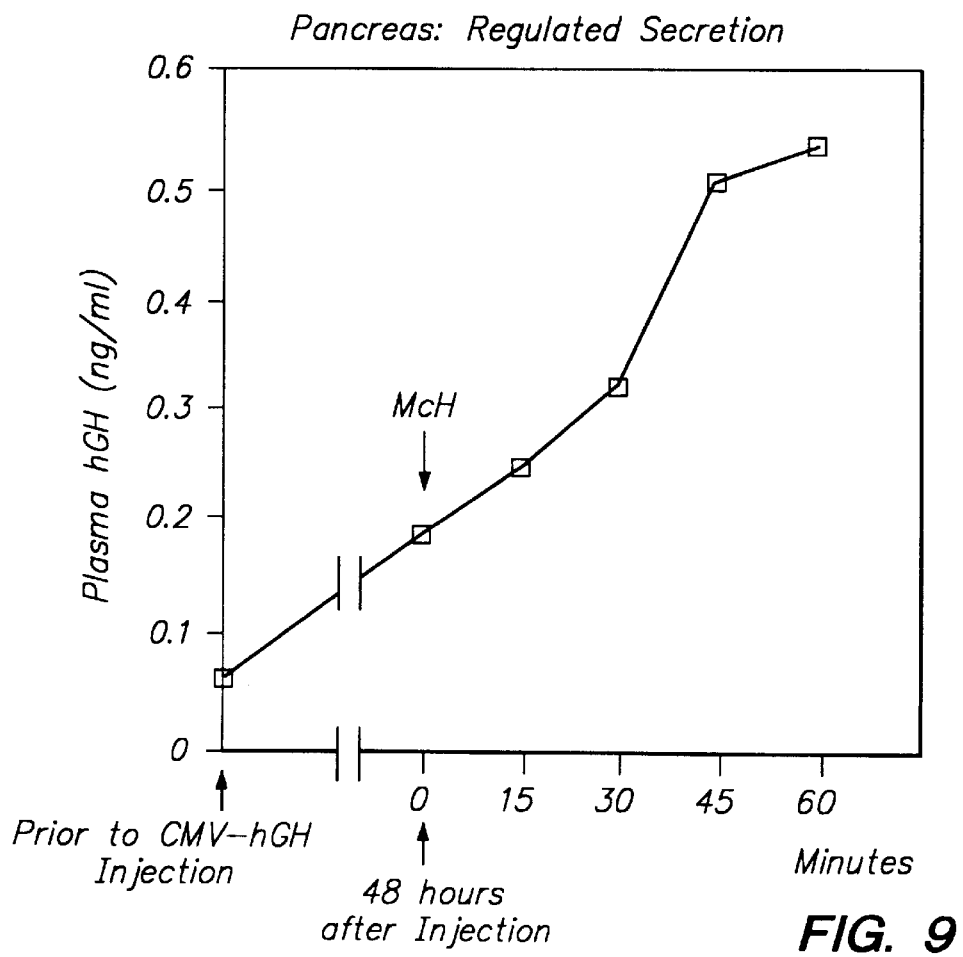
FIG. 9 is a graph showing regulation of plasma levels of hGH expressed from transformed pancreatic cells.

As shown in FIG. 9 (one representative animal) plasma levels of hGH increased markedly following McH injection, demonstrating that secretion of hGH expressed by transformed pancreatic cells is regulated by agonist stimulation. Moreover, bloodstream-directed secretion of hGH from the transformed pancreatic cells occurred at relevant, physiological levels useful in therapeutic administration (i.e., at the ng/ml level).

EXAMPLE 3

In Vivo Transformation of Salivary Glands by Retrograde Ductal Injection of DNA Encoding Human Growth Hormone Twelve adult rats weighing approximately 300 g each were anesthetized with an intraperitoneal injection of sodium pentobarbital. A total volume of 50 µl containing 4 µg of the pFGH.CMV plasmid, which contains cDNA encoding human growth hormone (hGH) (FIG. 2), was introduced into each submandibular gland of 8 rats by retrograde ductal injection via the ducts leading from the oral mucosa to the salivary gland. Briefly, both the left and right Wharton's duct were cannulated intraorally with polyethylene (PE) 10 tubing, and the DNA injected into the duct system of each gland in a retrograde fashion (4 µg/50 µl of PBS). The material was kept in place for two minutes before normal flow was reestablished.

For three of these animals the DNA was mixed in a 6% solution of the cationic lipid Lipofectin (labeled "liposomes") from Life Technologies (Gaithersburg, Md.). For four of these animals, the DNA was mixed with a 1:50 dilution of replication-defective human adenovirus (Ad5-di 342) supernatant. Control rats (4 rats) received 50 µl 0.9% saline (control) without plasmid. No significant leakage of material or bleeding occurred. After 3 hours, the animals were awake, drinking water, and appearing normal.

Approximately 48 hours after cDNA injection, the animals were sacrificed. The right and left submandibular glands were removed and were homogenized in cold 0.2 M (pH 8.0) sodium phosphate buffer (1:10 w/v) containing the protease inhibitors aprotinin, leupeptin, pepstatin, and PEFABLOC SC™. Homogenization was completed by shearing after 10 passes with a motorized pestle at approximately 4000 rpm in a glass homogenizer. The homogenates were centrifuged at 1000 g for 15 min, and the supernatant collected and stored at −80° C. until analysis. The levels of hGH in the protein samples were measured using the hGH radioimmune assay (Nichols Institute). Each assay was performed in duplicate and compared to a set of control samples.

Figure 7:
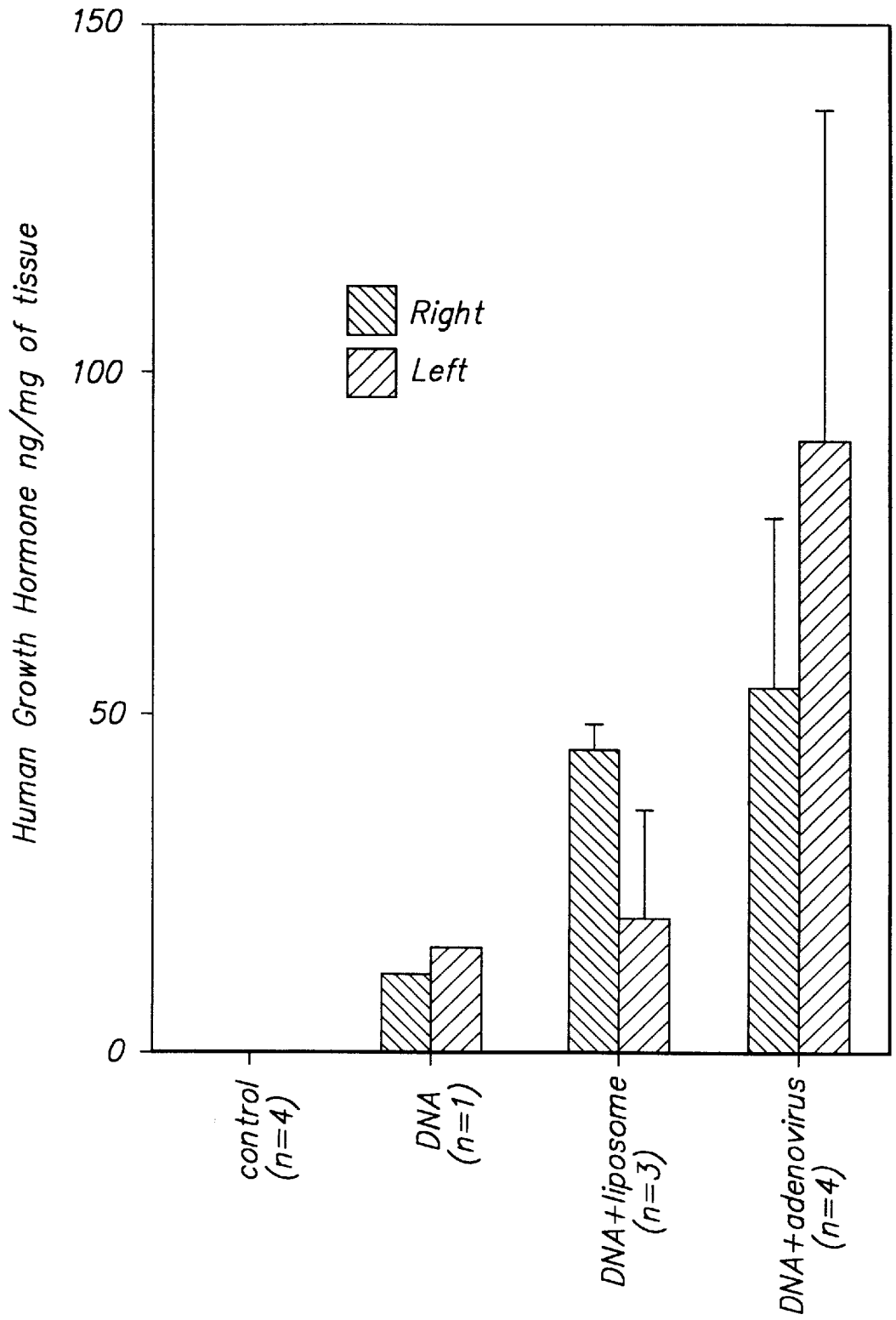
FIG. 7 is a graph showing tissue expression of hGH following transformation of salivary gland cells by intraductal injection.

Each of the submandibular glands of the rats injected with the pFGH.CMV vector expressed hGH in the salivary gland tissue; hGH expression was undetectable in the control rats' salivary glands (FIG. 7).

EXAMPLE 4

In Vivo Transformation of Salivary Glands by Retrograde Ductal Injection of hGH-Encoding DNA and Regulation of hGH Secretion Three adult rats weighing approximately 300 g each were anesthetized with an intraperitoneal injection of sodium pentobarbital. A control blood sample (prior to DNA) was drawn from the femoral vein of each animal. A total of 4 µg of the hGH-encoding plasmid pFGH.CMV (FIG. 2) in 50 µl, was introduced into each submandibular gland of each rat by retrograde ductal injection via the ducts leading from the oral mucosa to the salivary gland as described above in Example 2. No significant leakage of material or bleeding occurred. After 3 hours, the animals were awake, drinking water, and appearing normal.

Forty-eight hours after cDNA injection, the animals were again anesthetized and a control blood sample was drawn from the femoral vein of each animal (unstimulated serum level). The cholinergic agonist acetyl-β-methyl choline McH) was injected subcutaneously at 0.8 mg/kg body weight into each animal. Blood samples were collected from the femoral vein of each animal at 10 min, 20 min, 40 min, and 50 min after McH injection. Serum was separated from the blood of all samples after clotting, and kept at −20° C. prior to assay.

Figure 8:
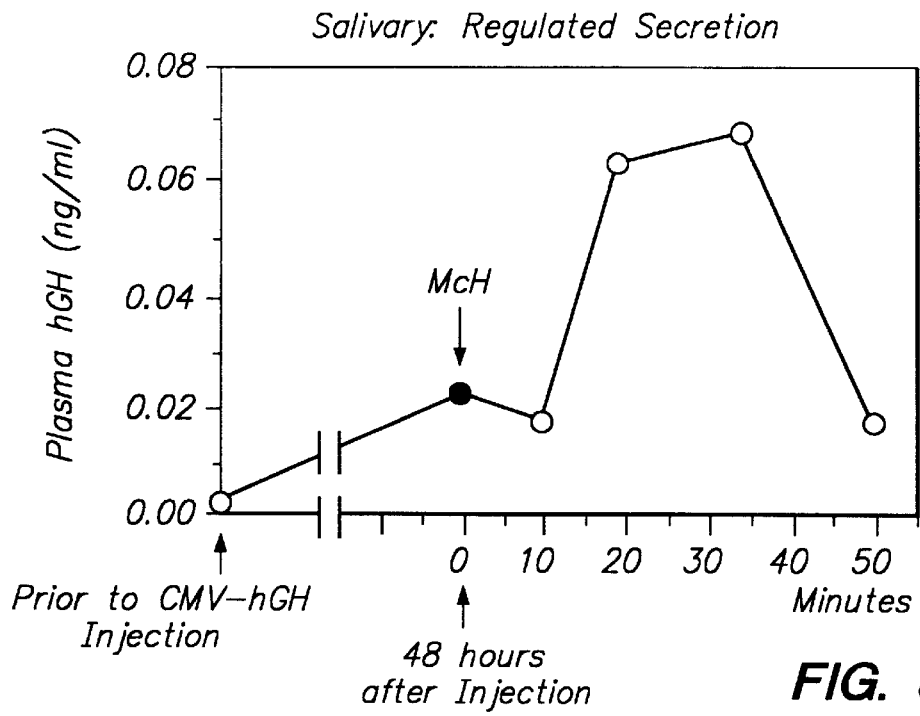
FIG. 8 is a graph showing regulation of plasma levels of hGH expressed from transformed salivary gland cells.

As shown in FIG. 8 (one representative animal), secretion of hGH into the bloodstream was dramatically increased in response to administration of McH, peaking at 40 min. Thus, these data demonstrate that introduction of hGH-encoding DNA into the salivary gland results in bloodstream-directed secretion of hGH and regulation by cholinergic stimulation. Moreover, regulation is at the level of secretion, not transcription, since transcriptional regulation would not result in increased hGH bloodstream levels in such a short period.

EXAMPLE 5

Figure 10:
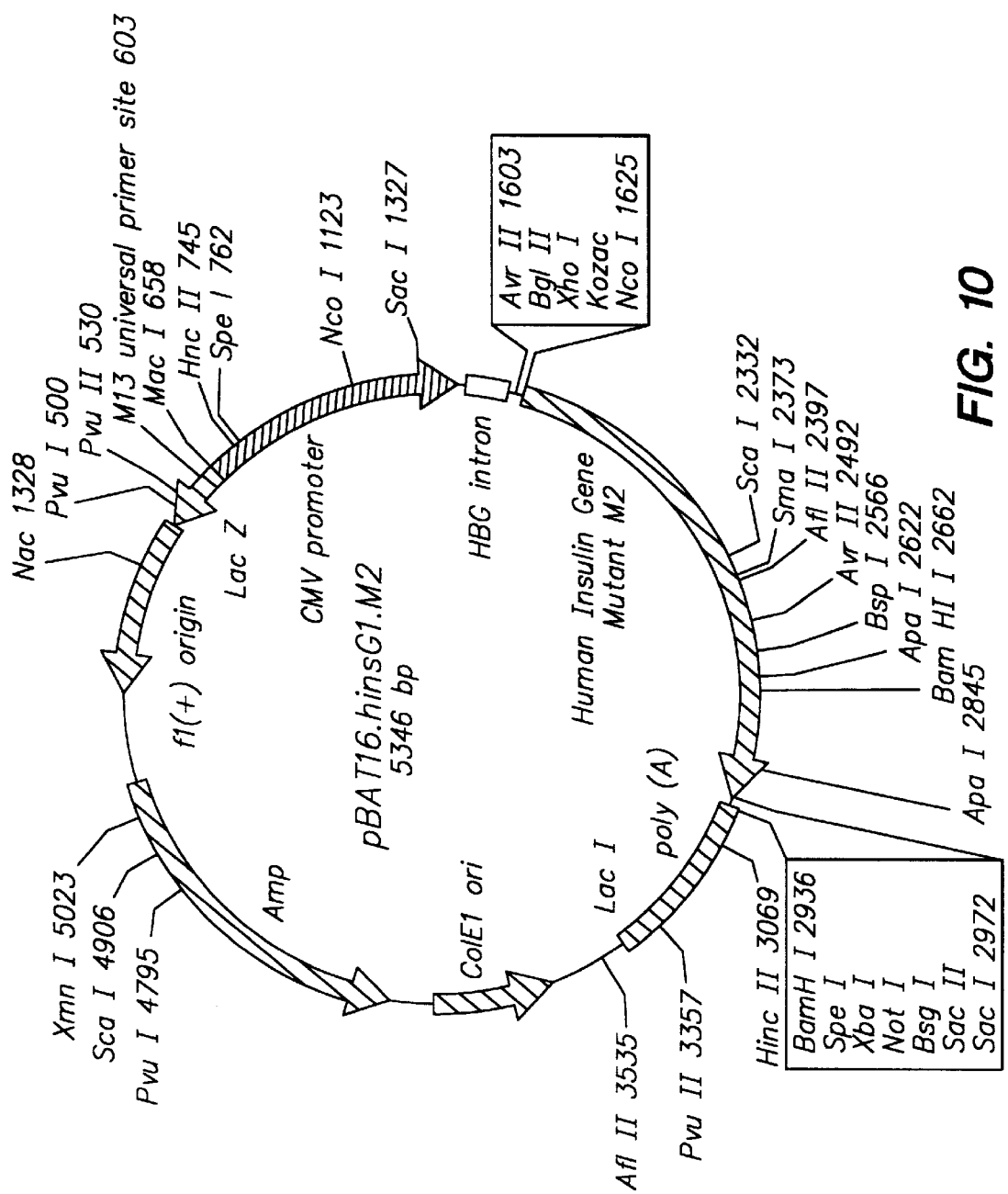
FIG. 10 is a map of the pBAT16.hInsG1.M2 construct, which contains DNA encoding an altered form of human insulin.

Treatment of Diabetes Mellitus Over a Three Day Period by In Vivo Transformation of Pancreatic Cells by Retrograde Ductal Injection with Insulin-Encoding DNA Streptozotocin, which induces diabetes mellitus in rats, was administered to 8 male Sprague-Dawley rats (260–280 g) after overnight fasting by intraperitoneal injection in 1 mM citrate buffer (pH 4.5) (Sigma) at 65 mg/kg of body weight. One hour later, animals were anesthetized with Nembutal and the body cavity opened to expose the gastrointestinal tract. Each animal was given the appropriate DNA construct directly by retrograde injection in the pancreatic duct in a 100 µl injection volume containing 8 µg DNA plus adenovirus (Ad5-di 342)($3\times10^{10}$ viral particles) as described above. Test animals (4 rats) received the human insulin-encoding construct pBat16.hInsG1.M2. The pBAT16.hInsG1.M2 construct (FIG. 10) encodes an insulin gene containing a site-directed mutation of the second protease site to create a furin recognition site; this construct provides for enhanced expression of processed insulin in non-neuroendocrine cells. In addition, the human β-globin first intron replaces the first insulin gene intron which is inefficiently spliced. Control animals (4 rats) received the control construct CMV-GFP, which contains a green fluorescent protein (GFP)-encoding sequence operably linked to a CMV promoter. The animals recovered fully and rapidly from the surgery without obvious side effects. Body weight and blood glucose were monitored daily for three days post-injection. Blood glucose was measured by the glucose oxidase method (Lifescan, Milpitas, Calif.).

Figure 11:
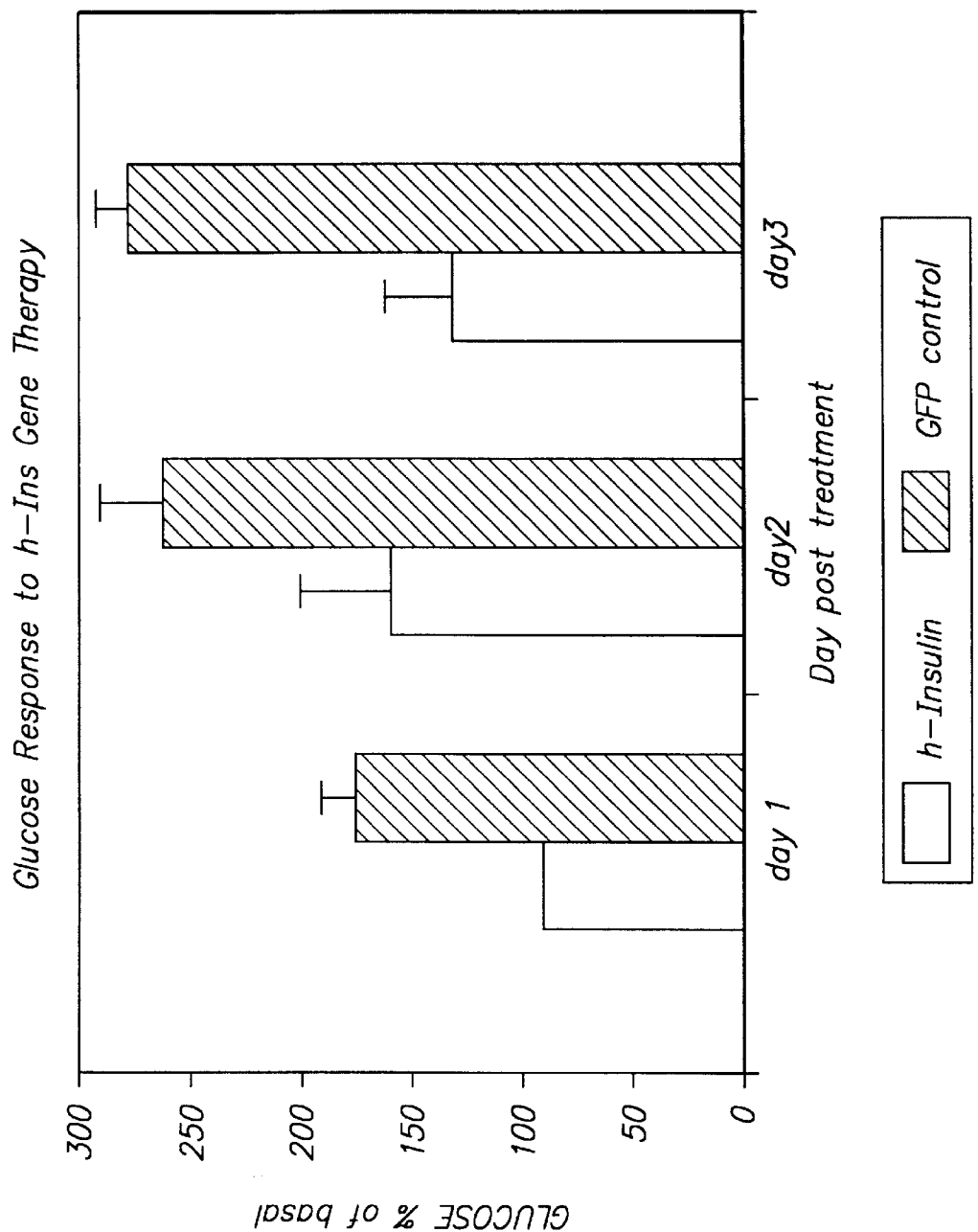
FIG. 11 is a graph showing the glucose response in streptozotocin-treated rats having pancreatic cells transformed with either human insulin (open bars) or green fluorescent protein (GFP; striped bars).

As shown in FIG. 11, treatment of the streptozotocin-induced diabetic rats with the insulin-encoding construct resulted in maintenance of almost complete euglycemia for 3 days. In contrast, control animals that received the GFP-encoding construct remained hyperglycemic throughout the test period. The data show that introduction of insulin-encoding DNA into the pancreas results in pancreatic cell transformation, as well as secretion of insulin by the transformed pancreatic cells at levels sufficient to overcome diabetes in an animal model. Moreover, these results show that the method of the invention provides regulated and relatively normal blood glucose levels. Surprising, the exocrine pancreas regulates the release of insulin such that blood sugar levels are maintained at regulated levels (normally the endocrine pancreas is responsible for regulation of bloodstream-directed secretion).

EXAMPLE 6

Treatment of Diabetes Mellitus Over a Six Day Period by In Vivo Transformation of Pancreatic Cells by Retrograde Ductal Injection with Insulin-Encoding DNA Streptozotocin was administered to 14 rats at 70 mg/kg body weight by intraperitoneal injection to induce diabetes mellitus. The animals were then anesthetized by intraperitoneal injection of sodium pentobarbital. Two rats did not receive streptozotocin and served as one negative control. Insulin-encoding DNA in the pBAT16.hInsG 1.M2 construct (FIG. 10) was administered to 8 of the streptozotocin-injected rats by retrograde ductal injection as described above. Six streptozotocin-treated rats received either 100 μl of saline without DNA (2 animals) or a control DNA without the human insulin gene (4 animals) by pancreatic retrograde ductal injection as additional negative controls. The animals recovered fully and rapidly from the surgery without obvious side effects. Blood samples were collected from the femoral vein of each animal at 24 hr intervals for 6 days. Human insulin was measured using a double antibody radioimmunoassay (Linco Laboratories, Saint Louis, Mo.).

Figure 12:
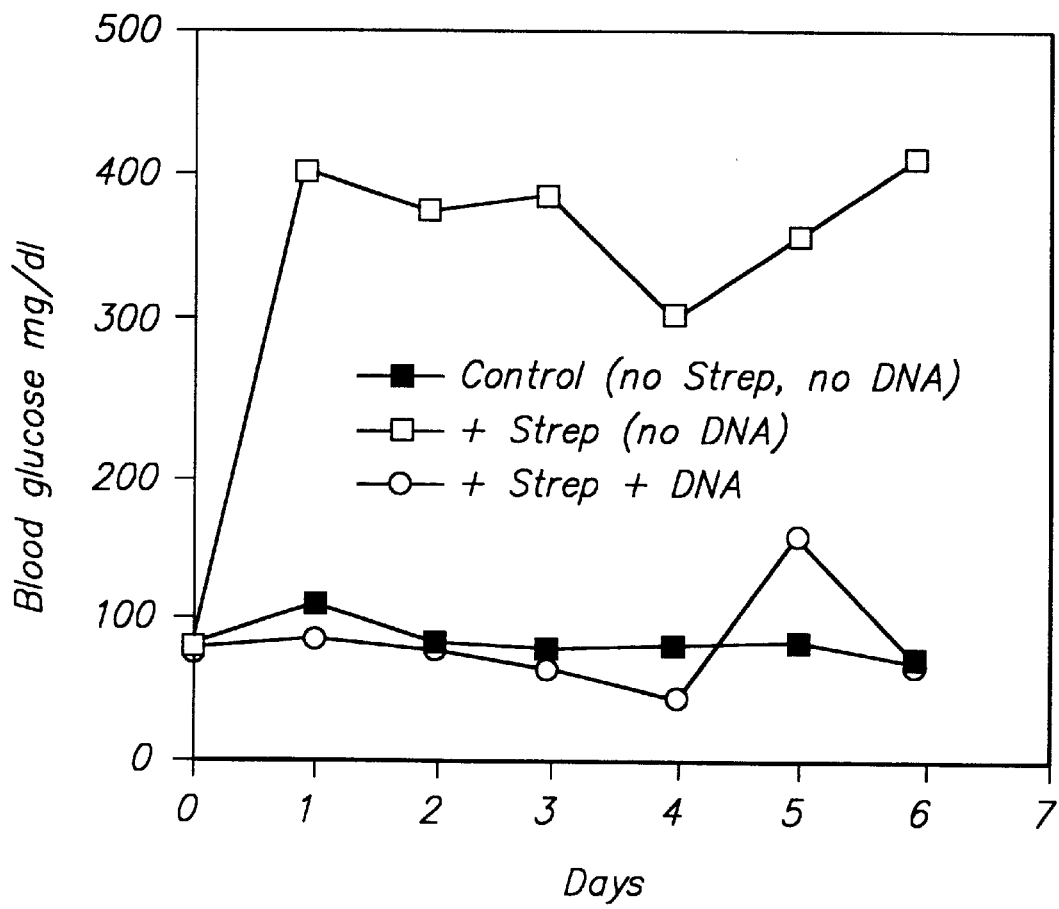
FIG. 12, is a graph showing the blood glucose levels in control rats (mock-treated; closed squares), streptozotocin-treated rats (open squares), and streptozotocin rats treated by transformation of pancreatic cells with DNA encoding human insulin (closed circles).

As shown in (FIG. 12), blood glucose levels were significantly decreased in the diabetic rats that received the insulin-encoding DNA (+Strep, +DNA) relative to diabetic the rats that received no DNA (+Strep, No DNA). Furthermore, these decreased blood glucose levels were observed throughout the entire 6 day course of the experiment. Thus, these data show that introduction of insulin-encoding DNA into the pancreas results in persistent expression of insulin, and that the insulin expressed by the transformed pancreatic cells is secreted into the bloodstream and can function in regulation of blood glucose at levels sufficient to overcome diabetes in an animal model. As shown in FIG. 12, elevated insulin levels for such an extended period additionally demonstrate prolonged expression from the DNA introduced into the pancreatic cells.

EXAMPLE 7

In vivo Transformation of Pancreatic Cells by Retrograde Ductal Injection of Green Fluorescent Protein-Encoding DNA and Expression in Pancreatic Cells To identify the pancreatic cells that expressed the recombinant protein, DNA encoding green fluorescent protein (GFP) was used to transform pancreatic cells according to the methods of the invention. EGFP cDNA from plasmid pEGFP.C2 (Clontech) was inserted into pFOX. The EGFP sequence was modified to contain an SV40 nuclear localization signal, in-frame at the 3' end. This addition allowed for partial nuclear localization and facilitated immunohistochemical detection. The CMV immediate early promoter was positioned upstream of the first intron of human β-globin to create the expression vector pFOX.EGFP.N2.CMV.

After fasting overnight, Male Sprague-Dawley rats (260–280 g) were anesthetized and the body cavity opened to expose the gastrointestinal tract. The green fluorescent protein (GFP)-encoding construct pFOX.EGFP.N2.CMV was administered to each animal by retrograde injection in the pancreatic duct in a 100 μl injection volume containing 8 μg DNA premixed with adenovirus ($3\times10^{10}$ viral particles) as described above. The animals recovered fully and rapidly from the surgery without obvious side effects.

Seventy-two hours post-treatment, the animals were sacrificed, and pancreases were removed and weighed (wet weight). Samples of each pancreas were fixed in 5% buffered formalin for 24–48 hours at room temperature. Fixed tissues were dehydrated and imbedded in paraffin, and 5 μm sections were processed for immunohistochemistry using standard techniques. Endogenous peroxidase was quenched in 0.7% $H_2O_2$/MeOH, and antigen retrieval was performed using Citra solution (Biogenex, San Ramon, Calif.) according to the manufacturers' instructions. Sections were preincubated for 30 minutes in 5% goat serum/phosphate-buffered saline (PBS), and then incubated overnight at 4° C. with primary antisera diluted in 5% goat serum/PBS.

The primary antisera were selected from either anti-GFP antisera (1:1500; Clontech, Palo Alto, Calif.), anti-insulin antisera (1:500; Dako, Carpenteria, Calif.), or non-specific rabbit sera (1:1500). The following day all sections were incubated with biotinylated goat anti-rabbit antiserum (5 μg/ml; Vector, Burlingame, Calif.) for 30 minutes at room temperature, and then incubated with streptavidin-aminohexanol-biotin horseradish peroxidase (HRP) complex (Vectastain-Elite, Vector). Protein was visualized by reaction with the peroxidase substrate 3,3-diaminobenzidine tetrahydrochloride (DAB; Sigma). The color reaction was followed by a brief counter stain in 1% methyl green (Sigma) prior to mounting. Negative controls included staining of sections from pancreas not injected with CMV-GFP, and omission of primary antiserum.

Staining for GFP was observed in the pancreas of animals treated with GFP DNA, but not in control animals. GFP expression was restricted to exocrine cells; there was no staining in either ductal or islet cells. Moreover, expression was observed in 0.1–1.0% of exocrine cells. Endogenous insulin was detected in adjacent sections; but GFP expression did not co-localize with insulin expression, suggesting that the pancreatic cells primarily transformed are exocrine, not endocrine cells. Under the conditions studied there was no histological indication of inflammatory infiltration as a consequence of ductal injection of the vector.

These data show that introduction of the DNA construct results in successful transformation of pancreatic cells, despite the introduction of the construct against the flow of pancreatic juices and the high concentrations of DNase in the pancreatic juice. Moreover, these data, combined with the data above showing that transformation of the pancreas results in bloodstream-directed secretion of the encoded protein, and suggest that transformation of exocrine pancreatic cells results in bloodstream-directed secretion of the protein encoded by the introduced construct. Furthermore, because insulin staining and GFP staining did not co-localize, introduction of the GFP-encoding construct resulted in transformation of exocrine tissue, which is normally associated with protein secretion into the gastrointestinal tract, rather than endocrine tissue, which is normally associated with bloodstream-directed secretion. Despite this, bloodstream-directed secretion was still obtained at physiologically relevant levels sufficient to treat diabetes mellitus in an animal model as evidenced in the examples above.

EXAMPLE 8

In Vivo Transformation of Liver Cells by Retrograde Ductal Injection of hGH-Encoding DNA and Bloodstream-Directed hGH Secretion Four rats were anesthetized and control blood samples (no DNA) were collected from the femoral vein of each animal. Transfection of liver cells was accomplished by exposing the duodenum by laparotomy and identifying the liver and the associated common bile duct. The common bile duct was cannulated either extraduodenally or through the papilla of Vater. The tubing was advanced to the bifurcation of the hepatic duct in order to prevent injected material from entering the distally located pancreatic drainage. A 1:50 dilution of replication-defective human adenovirus supernatant in 100 $\mu$l of phosphate-buffered saline (PBS) containing 8 $\mu$g of the hGH-encoding plasmid pFGH.CMV (FIG. 2) or 100 $\mu$l of PBS alone (no DNA) were slowly infused into the hepatic duct in a retrograde direction. The solution was left in place for approximately 2 min to 5 min before secretory flow was allowed to resume and the pancreatic duct blockage removed. The catheter was left in place and inserted into the duodenum through a small hole to ensure adequate biliary and pancreatic flow post-operatively. The abdomen was then closed with sutures. The animals recovered fully and rapidly from the surgery without obvious side effects.

Figure 13:
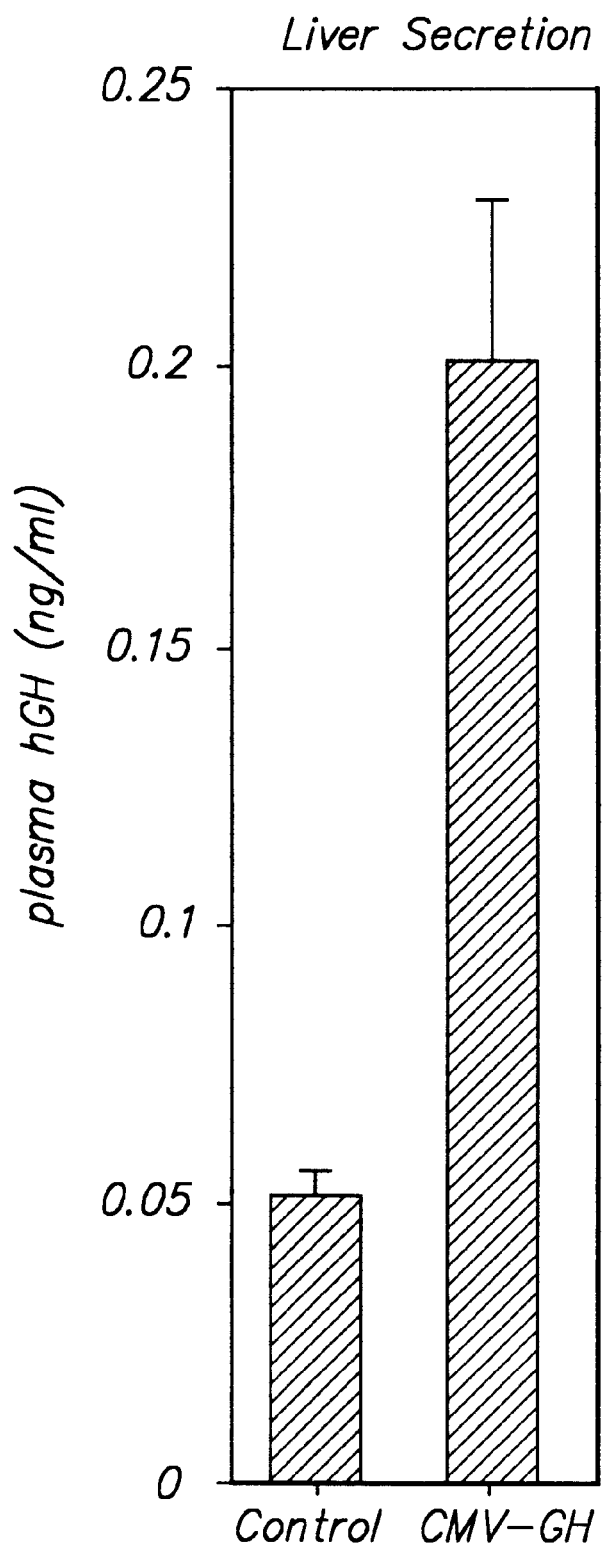
FIG. 13 is a graph showing expression of hGH in the plasma of control rats (no DNA) and of rats in which hGH-encoding DNA was introduced into the liver by intraductal injection.

Plasma hGH levels were measured 2 days after treatment; the results are shown in FIG. 13. Each data point in FIG. 13 represents the mean±standard error of the mean (SEM) for three animals. These data demonstrate that liver cells were transformed with the hGH-encoding DNA. Furthermore, hGH was secreted by the transformed liver cells into the bloodstream at physiologically relevant levels.

EXAMPLE 9

In Vivo Transformation of Pancreatic Cells with hGH-Encoding DNA and Expression in Rat Exocrine Pancreas and Plasma Following overnight fasting and anesthesia with pentobarbital, the abdominal cavity of the rats was opened and the pancreatic duct cannulated external to the duodenum with PE 10 tubing as described above. Eight to twenty-five micrograms of each of pFGH (promoter less construct), pFGH.chymo (construct with the chymotrypsin promoter), pFGH.RSV (construct with the RSV promoter), and pFGH.CMV (construct with the CMV promoter) was injected in a total volume of 100 $\mu$l of PBS into the pancreas via the pancreatic duct as described above. Immediately prior to injection construct samples were optionally premixed with either Lipofectin (6–12% vol:vol) or adenovirus ($3 \times 10^{10}$ viral particles). The material was kept in the duct for 5 min prior to establishing normal flow. The abdomen was the closed and the animals allowed to recover.

Forty-eight hours later the pancreas was harvested, plasma obtained, and human growth hormone measured. The animals were anesthetized, blood samples taken (either from the femoral vein or inferior vena cava), and the transfected tissue removed. The tissue was homogenized in PBS containing 5 mM Na2HPO$_4$ (pH 7.8) at a tissue to fluid ratio of 1:10 using a motorized mortar and pestle. Large particulate material in the homogenate was removed by sedimentation at 10,000× g for 30 minutes, and the supernatant assayed for the protein of interest. The results are shown in FIGS. 14–17. All data shown are the mean±the SEM.

Figure 14:
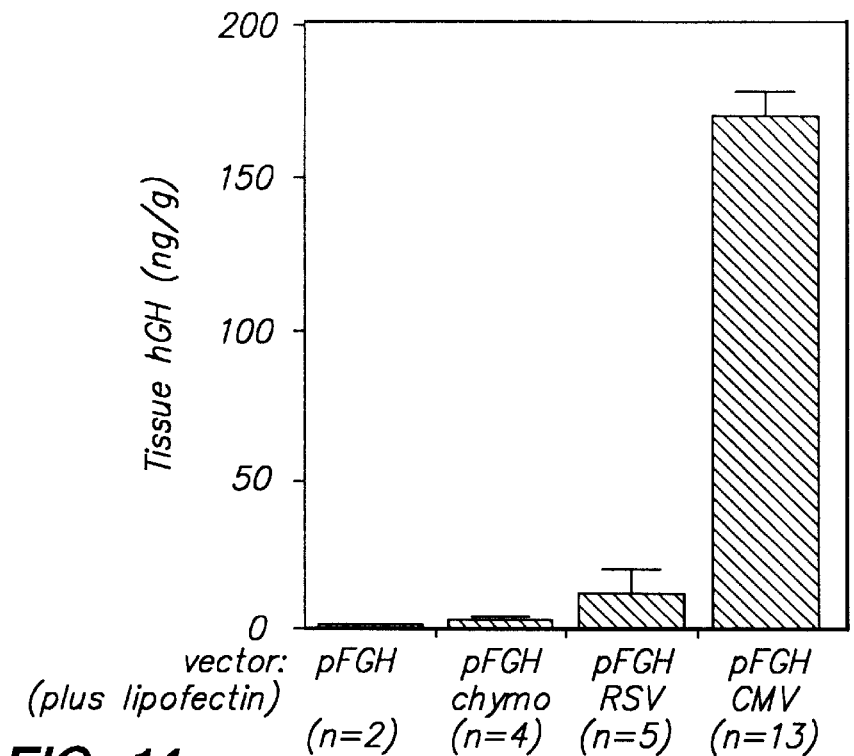
FIG. 14 is a graph showing the relative amounts of hGH in the pancreatic tissue of rats that received either pFGH (control), pFGH.chymo, pFGH.RSV, pFGH.RSV, or pFGH.CMV by intraductal administration to the pancreas.
Figure 15:
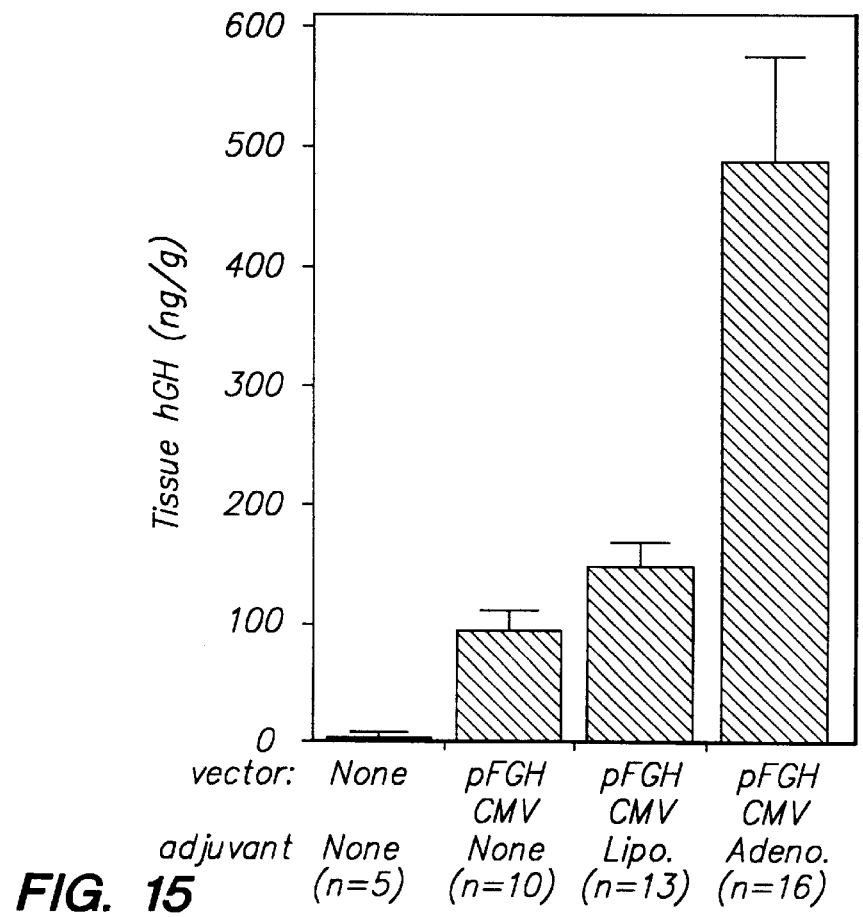
FIG. 15 is a graph showing the relative amounts of hGH in the pancreatic tissue of rats that received either no DNA (mock-transformed), pFGH.CMV, pFGH.CMV premixed with lipofectin, or pFGH.CMV premixed with adenovirus.

The effects of the various promoters upon tissue expression and secretion of hGH into the bloodstream are shown in FIGS. 14 and 15, respectively. In these experiments, the constructs were mixed with lipofection prior to administration. Of the promoters tested, the CMV promoter was by far the most effective, and produced high levels of hGH in tissue (in the range of 150 ng/g tissue wet weight) when compared to either promoter less controls, or plasmids containing RSV and chymotrypsin promoters (FIG. 14). The cationic lipid adjuvant Lipofectin increased expression by about 50%, and pre-mixing the plasmid with adenovirus enhanced tissue expression five fold (FIG. 15). Expression of hGH at 24, 48 or 72 hours after injection was similar under all conditions studied.

Figure 16:
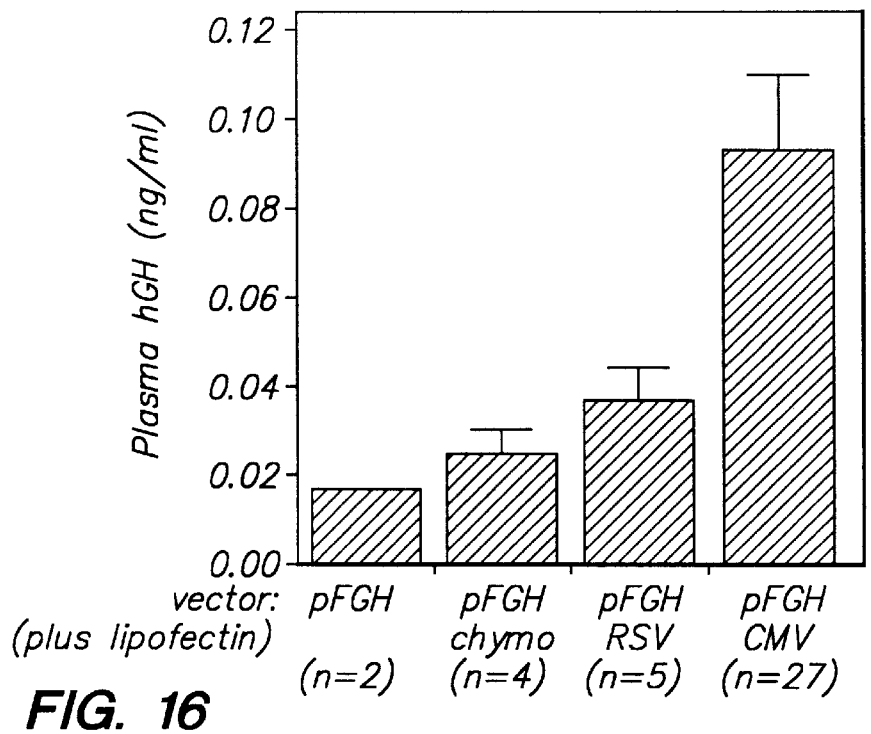
FIG. 16 is a graph showing the relative levels of plasma hGH in rats that received either pFGH (control), pFGH.chymo, pFGH.RSV, pFGH.RSV, or pFGH.CMV by intraductal administration to the pancreas.
Figure 17:
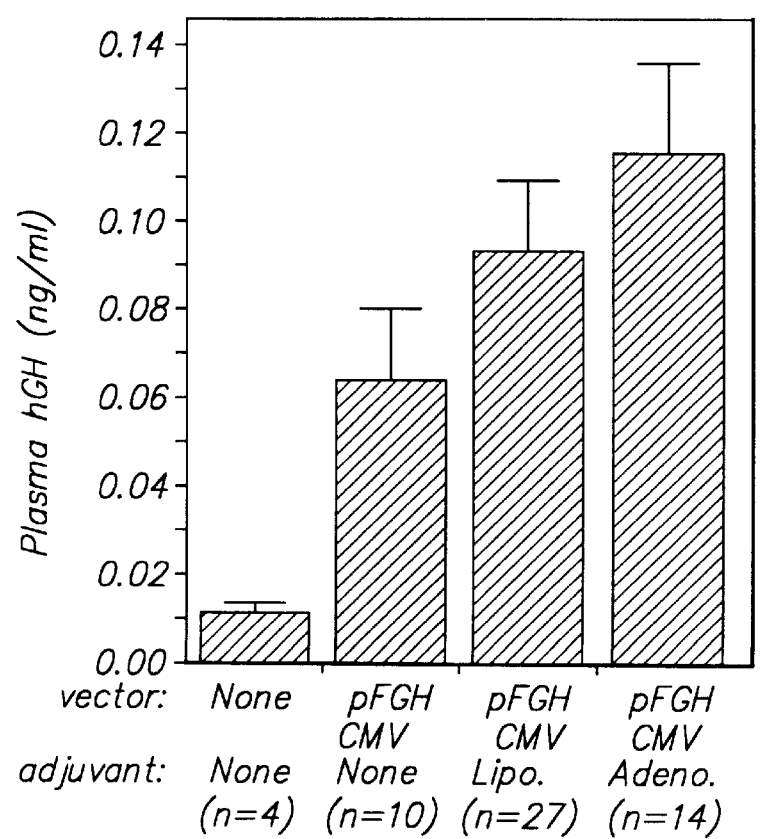
FIG. 17 is a graph showing the relative amounts of plasma hGH in rats that received either no DNA (mock-transformed), pFGH.CMV, pFGH.CMV premixed with lipofectin, or pFGH.CMV premixed with adenovirus by intraductal administration to the pancreas.

As shown in FIGS. 16 and 17, hGH was secreted into plasma. Plasmids containing the CMV promoter increased circulating levels of hGH five times above background (FIG. 16). With plasmid alone, plasma hGH concentrations in the range of 60 to 80 pg/ml were routinely observed. Premixing the plasmids with adjuvants also increased circulating hGH levels (FIG. 17). Lipofectin increased plasma levels by an additional 50%, and adenovirus by 75%, when compared to plasmid alone.

EXAMPLE 10

Comparison of hGH Secretion by Rat Liver, Pancreas, and Combined Liver and Pancreas Transformed with hGH-Encoding DNA Eight micrograms of the pFGH.CMV construct premixed with adenovirus as described above in Example 9, was injected into the ducts of either the liver, the pancreas, or both organs of the same animal. Where only the liver or the pancreas was transformed (liver alone or pancreas alone), the DNA was introduced according to the methods described above. Where both the liver and pancreas were transformed, the DNA-containing formulation was introduced into the hepatic duct first, and then the tubing partially withdrawn to provide access to the pancreatic duct system. A temporary ligature was then placed around the hepatic duct to prevent the second infusion from entering the parenchyma of the liver. Thus, animals in which both the pancreas and liver were transformed received two doses of the DNA-containing formulation. Plasma hGH levels were measured two days later.

Figure 18:
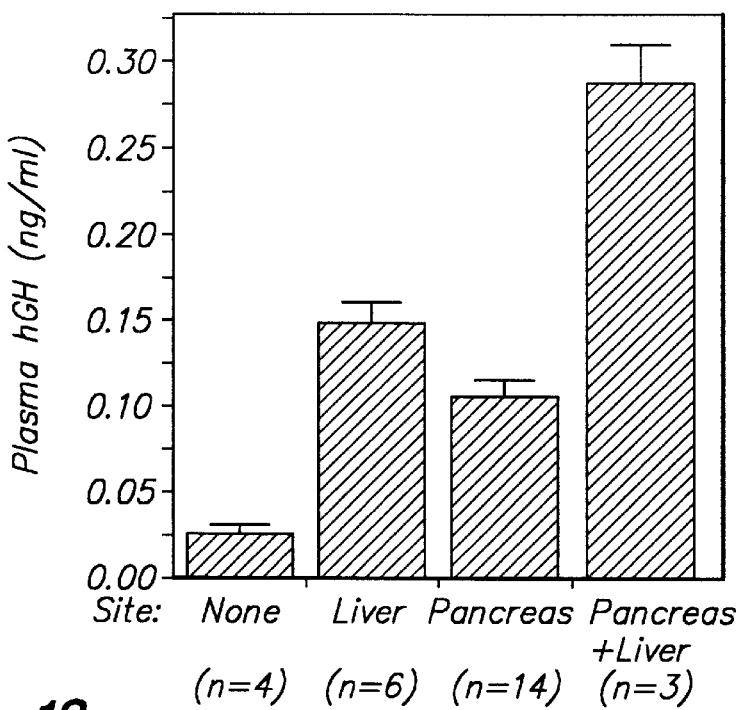
FIG. 18 is a graph showing the relative levels of plasma hGH in rats that received no DNA (control), received hGH-encoding DNA via intraductal delivery to the liver, received hGH-encoding DNA via intraductal delivery to the pancreas, or received hGH-encoding DNA via intraductal delivery to both the liver and pancreas.

In animals having transformed liver (liver alone) or pancreas (pancreas alone), hGH was expressed in liver or pancreatic tissue, respectively, and hGH detected in plasma under both circumstances. Tissue levels in liver when transformed alone were far lower than in the pancreas when transformed alone (less than 1 ng/g, as compared to about 500 ng/g), but hGH concentration in plasma of animals in which only the liver was transformed was nonetheless comparable to hGH plasma levels in animals having only the pancreas transformed (in the range of 0.15 ng/ml; FIG. 18). These results are consistent with the observation that, in contrast to the exocrine cells of the pancreas and salivary glands, hepatocytes secrete most of what they produce soon after synthesis.

Figure 19:
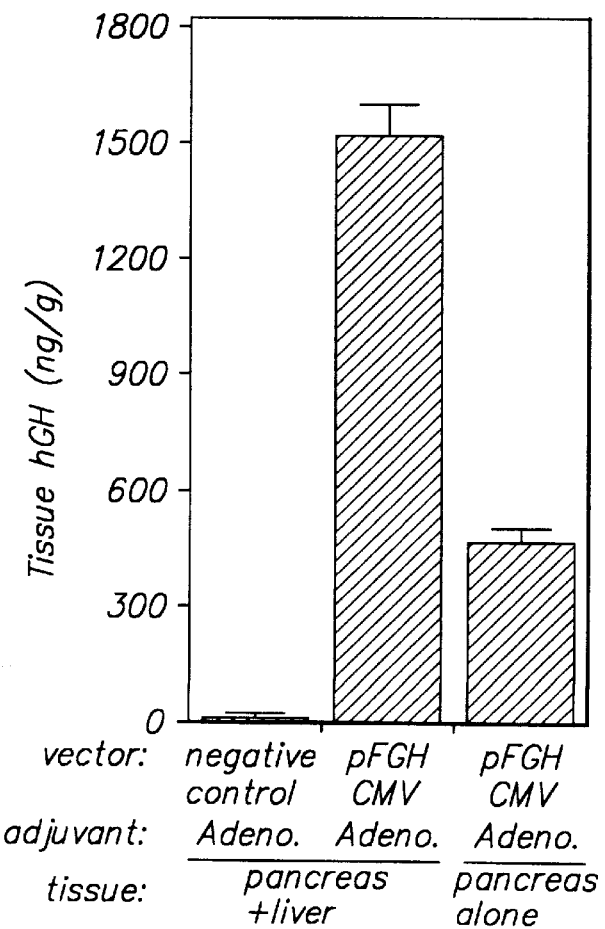
FIG. 19 is a graph showing the relative levels of hGH expression in pancreas tissue following administration of DNA to both pancreas and liver or to pancreas alone. The graph shows tissue levels of hGH after administration of a control (no DNA) to both pancreas and liver (left-most bar); administration of pFGH.CMV to both pancreas and liver (center bar); and pFGH.CMV to pancreas alone (right-most bar). Adenovirus was admixed with the construct as an adjuvant.

When pancreas and liver were both transfected, plasma levels were higher than seen when the glands were treated individually (nearly 0.3 ng/ml)—a value approximately equal to the sum of that observed for the two organs separately. Surprisingly, transformation of both liver and pancreas resulted in tissue levels in the pancreas being significantly increased relative to tissue levels in the pancreas when the pancreas was transformed alone (FIG. 19).

EXAMPLE 11

Human growth hormone (hGH) expression in rat salivary gland.

Four micrograms of the pFGH.CMV construct, premixed with either Lipofectin or adenovirus, was injected into each submandibular gland via retrograde ductal injection (via Wharton's duct) as described above. Two days later, each gland was harvested and hGH content was measured.

Figure 20:
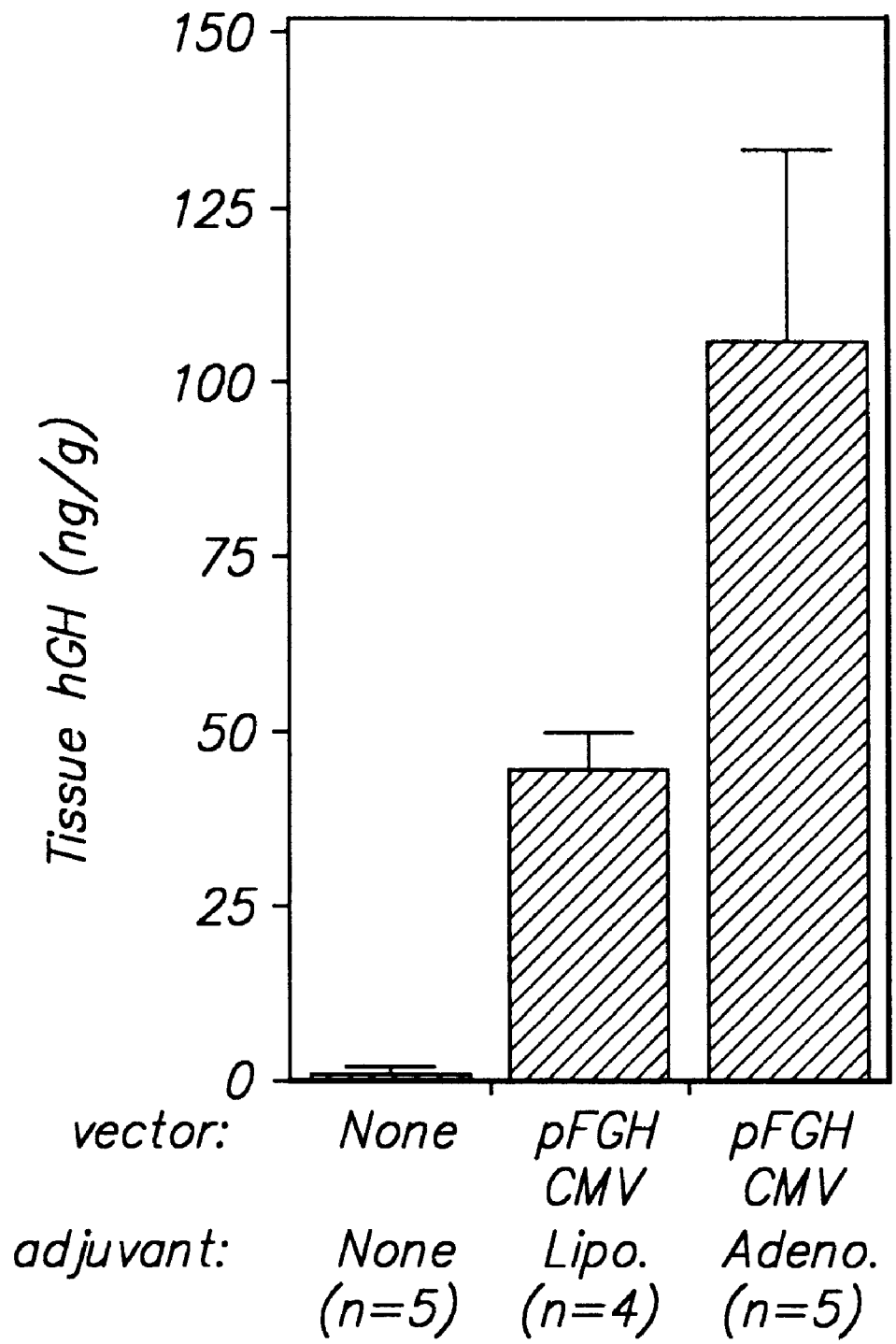
FIG. 20 is graph showing the relative levels of hGH expression in salivary gland tissue in rats that received either no DNA (control rats), pFGH.CMV, pFGH.CMV premixed with lipofectin, or pFGH.CMV premixed with adenovirus.

As shown in FIG. 20, tissue levels of hGH averaged about 50 ng/g tissue wet weight. Plasma hGH levels were in the 20–40 pg/ml range. As in the pancreas, the addition of adenovirus increased tissue hGH levels, in this case to 100 ng/g (FIG. 20).

EXAMPLE 12

Stimulation of Human growth hormone (hGH) secretion

Even when exocrine secretory cells store large amounts of protein, such as after a period of fasting, they secrete these proteins at a low rate under unstimulated conditions (i.e. basal or constitutive secretion). Greater rates are achieved when exogenous stimulants (e.g., hormonal stimulants and/or stimulation associated with eating) are applied. To determine whether secretion of the engineered protein would be enhanced during feeding, pancreatic secretion was stimulated with a secretory stimulant. For these experiments we used animals in which both pancreas and liver were transfected. Eight micrograms of the pFGH.CMV construct were injected into ducts of both the pancreas and liver of four rats as described above. A blood sample was taken prior to injection as a control. Two days after transfection, a second control blood sample was taken and the rats were treated with the cholinergic agonist, acetyl-β-methylcholine (McH) (0.8 mg/kg body weight).

Figure 21:
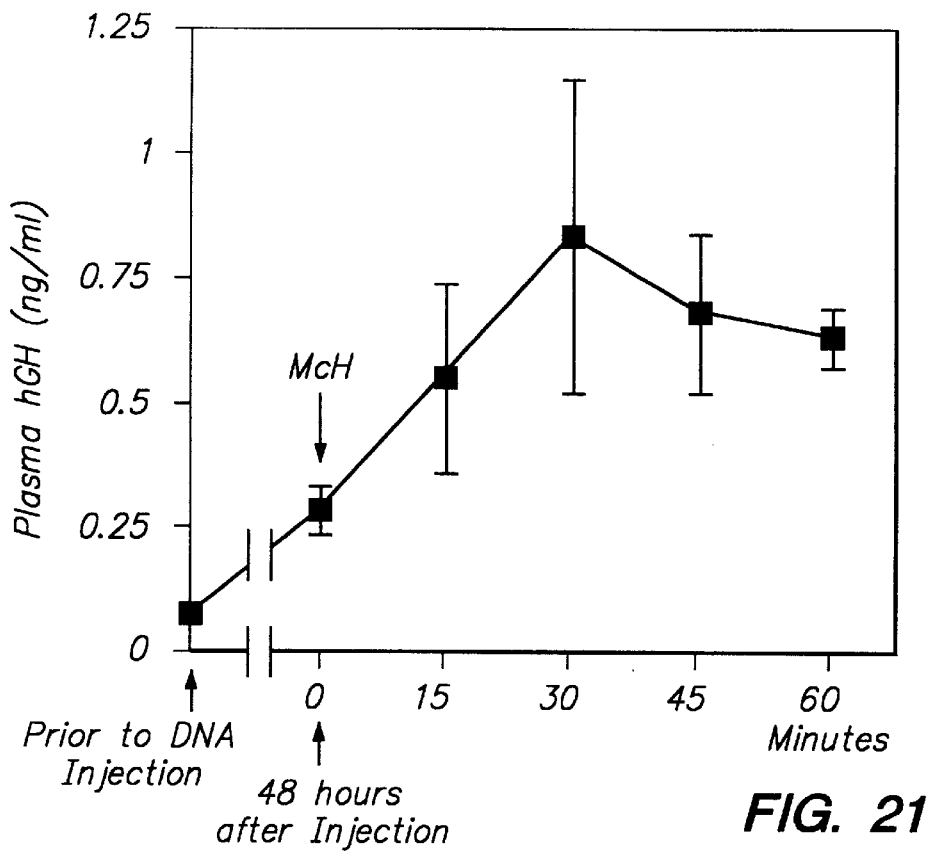
FIG. 21 is a graph showing stimulation of hGH secretion into the plasma of rats that received hGH-encoding DNA by intraductal injection into both the pancreas and liver.

As shown in FIG. 21, hGH secretion was increased three fold within 30 minutes of stimulation, with plasma levels approaching 1.0 ng/ml. Similar enhancement of hGH secretion was observed when either the pancreas was studied alone, or when the salivary glands were studied alone. These data show that hGH secretion is enhanced by stimulation with a cholinergic agonist. Thus secretion of hGH is regulated in a manner similar to secretion of endogenous proteins.

Although the concentration of hGH in plasma was correlated to the level of hormone in the pancreas (r=0.55, p<0.01, n=41), at high tissue levels, plasma concentration was not linearly proportional to tissue content. For example, addition of adenovirus to the hGH vector produced a five fold increase in tissue levels relative to the plasmid alone (FIG. 20), but only about a two fold increase in plasma concentration (see, e.g., FIGS. 16 and 17, Example 9 above). This lack of proportionality indicates that it is not the concentration of product in the cells alone that determines the rate of secretion into blood, but that at high tissue levels, secretion is limited by other factors. This result is similar to what is observed for endogenous protein secretion and suggests that secretion of the engineered protein is regulated in much the same manner.

EXAMPLE 13

Human Insulin Expression and Secretion in Diabetic Rat Pancreas

In an attempt to treat a disease state, diabetes mellitus, we expressed human insulin in the exocrine pancreas. Fasted experimental and control animals received intra-peritoneal streptozotocin (Sigma; 65 mg/kg body weight, in 1 mM citrate buffer, pH4.5) on day zero one hour prior to administration of the insulin-encoding construct. The experimental animals subsequently received 8 μg of the insulin plasmid (pBAT16.hInsG1.M2) premixed with adenovirus and injected into the pancreatic duct, also on day zero. The pBAT16.hInsG1.M2 construct contains the human insulin cDNA linked to a CMV immediate early promoter, which is positioned upstream of the first intron of human β-globin. The human insulin cDNA was mutated to convert the second protease site, between peptides C and A, to a furin recognition site. This allows for correct proteolytic processing of mature insulin in non-endocrine cells.

Figure 22:
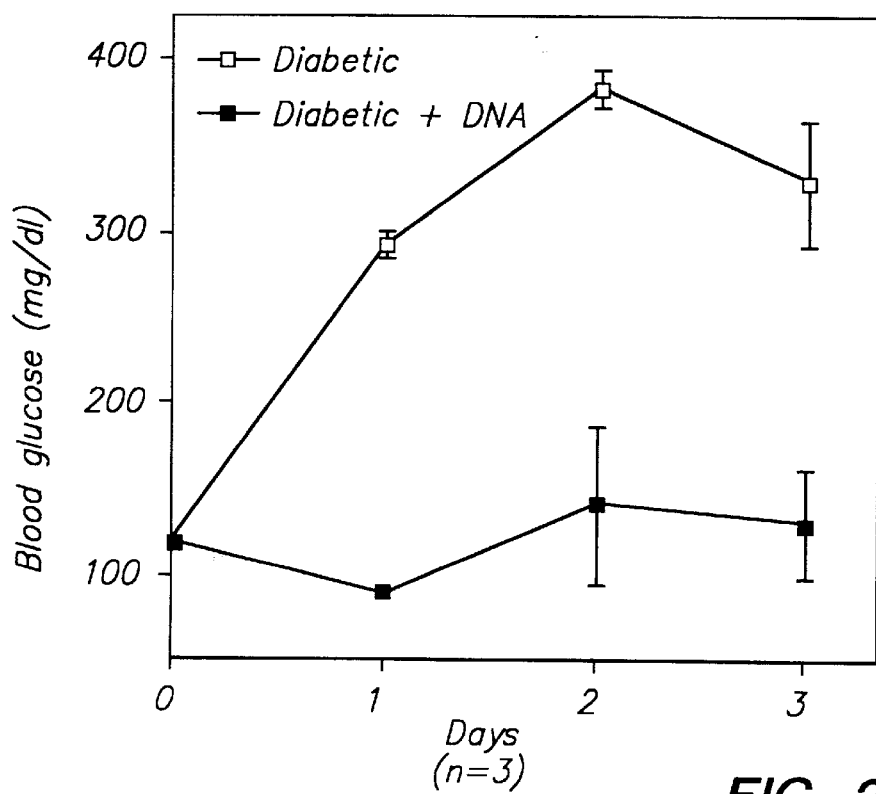
FIG. 22 is a graph showing the blood glucose levels of streptozotocin-treated rats (diabetic) that received either no DNA (open squares) or received human insulin-encoding DNA by intraductal injection into the pancreas (closed squares) over a three day period.
Figure 23:
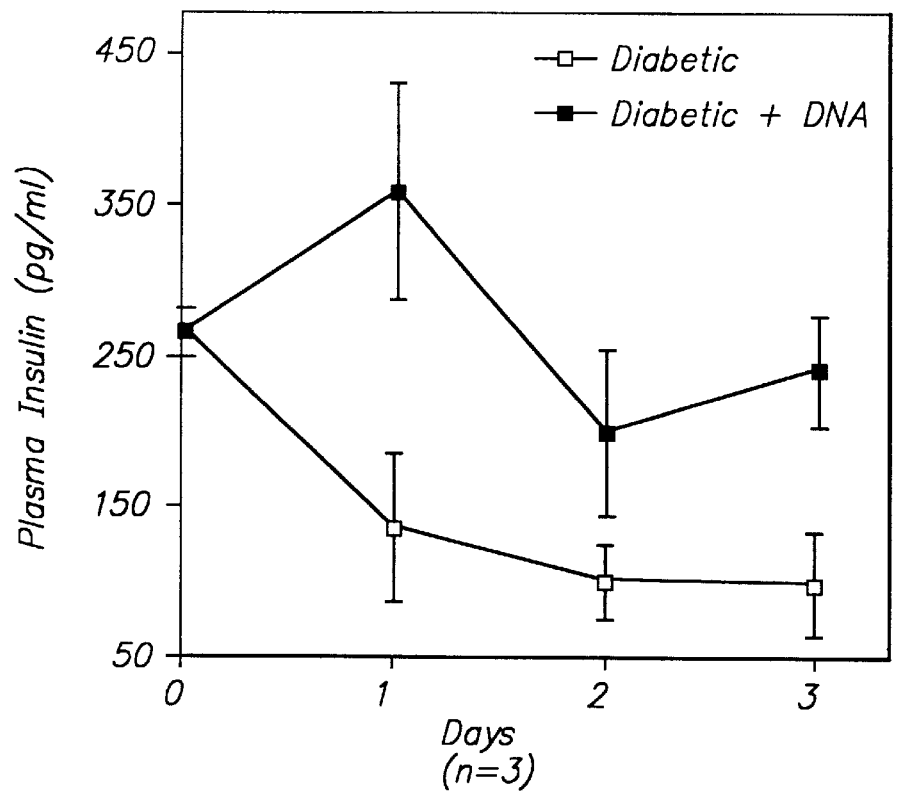
FIG. 23 is a graph showing the plasma insulin levels of streptozotocin-treated rats (diabetic) that received either no DNA (open squares) or received human insulin-encoding DNA by intraductal injection into the pancreas (closed squares) over a three day period.
Figure 24:
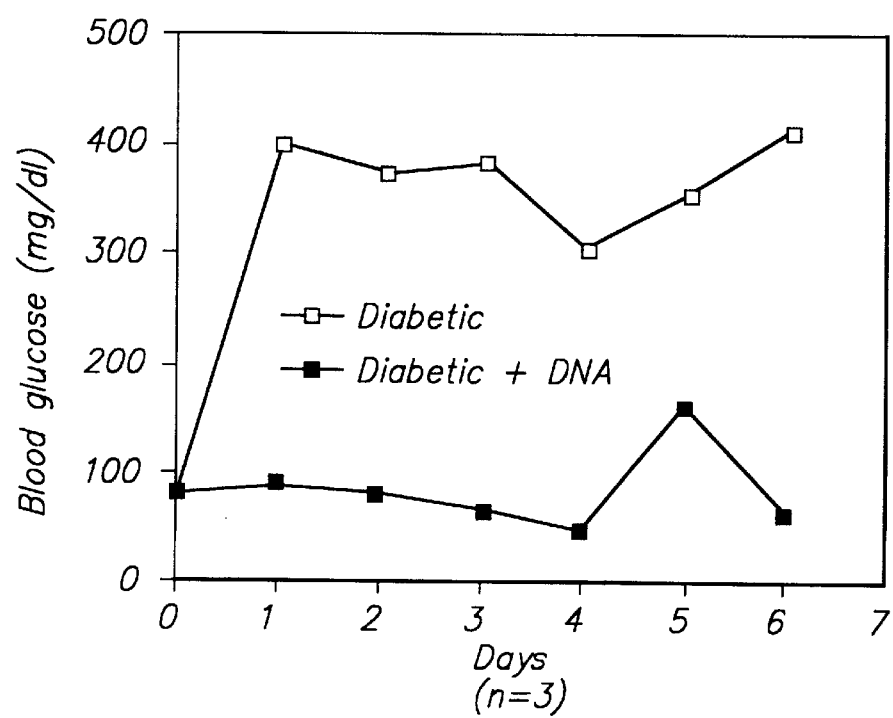
FIG. 24 is a graph showing the blood glucose levels (over a six day period) of streptozotocin-treated rats (diabetic) that received either no DNA (open squares) or received human insulin-encoding DNA by intraductal injection into the pancreas (closed squares).

Plasma insulin and glucose levels were determined for up to six days. Plasma glucose levels in diabetic rats (n=3), and diabetic rats treated with the pBAT16.hInsG1.M2 plasmid (n=3), measured over a three day period, are shown in FIG. 22. Plasma insulin levels in diabetic rats (n=3), and diabetic rats treated with the pBAT16.hInsG1.M2 plasmid (n=3), measured over a three day period, are shown in FIG. 23. Plasma glucose levels in individual diabetic (n=3) and pBAT16.hInsG1.M2 plasmid-treated diabetic rats (n=3), measured over a six day period, are shown in FIG. 24.

As a consequence of streptozotocin administration, blood glucose levels rose from the normal level of 100 mg/dl to 300–400 mg/dl within 24 hours and remained elevated for the duration of the study (FIG. 22). Treatment with the human insulin plasmid reduced blood glucose levels in diabetic rats to the normal range (FIGS. 22 and 24), and concentrations of insulin remained near pre-treatment values (FIG. 23). Blood glucose levels were euglycemic for the duration of the study (6 days; FIG. 24). Animals transfected with a control plasmid remained diabetic (data not shown). These data show that regulation of insulin secretion in response to feeding was effective.

EXAMPLE 14

In vivo gene transfer of DNA encoding human growth hormone by retrograde injection of DNA into the salivary gland A DNA expression construct encoding human growth hormone (hGH) is prepared by operably linking a CMV promoter to hGH-encoding DNA. The expression cassette is then inserted into a construct such as the bacterial plasmid pBR322. *Escherichia coli* is then transformed with the plasmid using conventional transformation procedures. *E. coli* containing the plasmid are selected by virtue of the tetracycline or ampicillin resistance encoded by pBR322, and the transformed bacterial cells propagated in culture. Plasmid DNA is then isolated from the transformed bacterial cell culture and the DNA purified by cesium gradient.

Approximately 250 µg of the purified plasmid DNA containing hGH DNA is injected into the salivary gland of a human patient by retrograde ductal injection via a salivary gland duct. Expression and intravenous secretion of the protein is assessed using the method described above.

EXAMPLE 15

In vivo gene transfer of DNA encoding human growth hormone by retrograde ductal injection of naked DNA into the pancreas A construct containing hGH-encoding DNA (Marshall et al., *Biotechnology* 24:293–298, 1992) operably linked to the CMV promoter is resuspended in 0.9% saline and a volume of the DNA solution is administered to a human patient. Approximately 1 mg of DNA is delivered to the pancreas of the patient by cannulation of the pancreatic duct by duodenal intubation using endoscopic retrograde cholangiopancreatography. Expression and secretion of human growth hormone into the bloodstream is assessed by detection of the protein in the patient's blood.

EXAMPLE 16

In vivo gene transfer of DNA encoding human insulin by cannulation of naked DNA into the liver A construct containing human insulin-encoding DNA operably linked to the CMV promoter is resuspended in 0.9% saline and a volume of the DNA solution is administered to a human patient. Approximately 1 mg of DNA is delivered to the patient's liver by cannulation of the hepatic duct. Expression and secretion of human growth hormone into the bloodstream is assessed by detection of the protein in the patient's blood.

EXAMPLE 17

In vivo gene transfer of human insulin-encoding DNA to both the pancreas and the liver of a patient A construct containing human insulin-encoding DNA operably linked to the CMV promoter is resuspended in 0.9% saline. A volume of the DNA solution is administered to a human patient so as to transform both pancreatic and hepatic cells (e.g., by introducing the DNA solution into the common bile duct before it splits into the hepatic and pancreatic ducts). Approximately 2 mg of DNA is delivered to the patient's liver by cannulation of the hepatic duct; in addition, approximately 1 mg of DNA is delivered to the pancreas via retrograde injection via the pancreatic duct. Expression and secretion of human growth hormone into the bloodstream is assessed by detection of the protein in the patient's blood.

Following procedures similar to those described above, other therapeutic proteins can be expressed from DNA inserted in the genome of a secretory gland cell by gene transfer according to the invention.

The invention now being fully described, it will be apparent to one of ordinary skill in the art that many changes and modifications can be made thereto without departing from the spirit or scope of the appended claims.

What is claimed is:

1. A method of reducing blood glucose levels in a diabetic mammalian subject, the method comprising:

introducing into the pancreas of the mammalian subject a construct comprising an insulin-encoding DNA and a promoter sequence operably linked to the insulin-encoding DNA to facilitate expression in a eukaryotic cell, said introducing being by intraductal administration;

wherein expression of the introduced construct in the pancreas occurs such that a biologically active insulin polypeptide is delivered into the bloodstream of the patient in a therapeutically effective amount, and blood glucose levels in the mammalian subject are reduced.

2. The method of claim 1, wherein a euglycemic state is maintained for at least three days.

3. The method of claim 1, wherein a euglycemic state is maintained for at least 6 days.

4. The method of claim 1, the method further comprising enhancing delivery of the insulin polypeptide to the bloodstream by administration of a cholinergic agonist to the mammalian subject.

5. The method of claim 1, the method further comprising enhancing delivery of the insulin polypeptide into the bloodstream by ingestion of a meal by the mammalian subject.

6. A method of delivering a desired polypeptide to a mammalian subject, the method comprising:

introducing in vivo into a lumen of a duct of a salivary gland and into a lumen of a duct of a liver of the mammalian subject a construct comprising a DNA of interest that encodes the desired polypeptide and a promoter sequence operably linked to the DNA of interest to facilitate expression in a eukaryotic cell;

wherein the introduced construct is expressed in each of the salivary gland and the liver such that the polypeptide is delivered into the bloodstream of the mammal from each of the salivary gland and the liver.

7. The method of claim 6, wherein the DNA of interest encodes a factor VIII polypeptide.

8. The method of claim 6, wherein the DNA of interest encodes a erythropoietin polypeptide.

9. The method of claim 6, wherein introduction into the salivary gland and into the liver is by retrograde ductal administration.

10. The method of claim 6, wherein the construct introduced into the salivary gland is not contained within a viral particle.

11. A method of delivering a polypeptide to a mammalian subject, the method comprising:

introducing in vivo into a lumen of a duct of a salivary gland and into a lumen of a duct of a pancreas of the mammalian subject a construct comprising a DNA of interest that encodes a desired polypeptide and a promoter sequence operably linked to the DNA of interest to facilitate expression in a eukaryotic cell;

wherein the introduced construct is expressed in each of the salivary gland and the pancreas such that the polypeptide is delivered into the bloodstream of the mammalian subject from each of the salivary gland and the pancreas.

12. The method of claim 11, wherein the desired polypeptide is selected from the group consisting of insulin, growth hormone, interferon-alpha 2b, Interferon-alpha 2a, interferon-alpha N1, filgastim, insulinotropin, imiglucerase, clotting factor VIII, interferon-beta1b, erythropoietin, sargramostim, interleukin-2, interferon-gamma, anti-CD3 antibody, GPIIb/IIIa monoclonal antibody, adenosine deaminase, interleukin-8, insulin-like growth factor-1, platelet-derived growth factor, epidermal growth factor, and hemoglobin.

13. The method of claim 11, wherein the DNA of interest encodes a human insulin polypeptide.

14. The method of claim 11, wherein the DNA of interest encodes a factor VIII polypeptide.

15. The method of claim 11, wherein the DNA of interest encodes a crythropoietin polypeptide.

16. The method of claim 11, wherein introduction into the salivary gland and into the pancreas is by retrograde ductal administration.

17. The method of claim 11, wherein the construct introduced into the salivary gland is not contained within a viral particle.

18. A method of delivering a polypeptide to a mammalian subject, the method comprising:

administering directly in vivo into a lumen of a duct of a pancreas and into a lumen of a duct of a liver of the mammalian subject a construct comprising a DNA of interest that encodes a desired polypeptide and a promoter sequence operably linked to the DNA of interest to facilitate expression in a eukaryotic cell;

wherein the introduced construct is expressed in each of the pancreas and the liver such that the polypeptide is delivered into the bloodstream of the mammal from each of the pancreas and the liver.

19. The method of claim 18, wherein the desired polypeptide is selected from the group consisting of insulin, growth hormone, interferon-alpha 2b, Interferon-alpha 2a, interferon-alpha N1, filgastim, insulinotropin, imiglucerase, clotting factor VIII, interferon-beta1b, erythropoietin, sargramostim, interleukin-2, interferon-gamma, anti-CD3 antibody, GPIIb/IIIa monoclonal antibody, adenosine deaminase, interleukin-8, insulin-like growth factor-1, platelet-derived growth factor, epidermal growth factor, and hemoglobin.

20. The method of claim 18, wherein the DNA of interest encodes a human insulin polypeptide.

21. The method of claim 18, wherein the DNA of interest encodes a factor VIII polypeptide.

22. The method of claim 18, wherein the DNA of interest encodes an crythropoietin polypeptide.

23. The method of claim 18, wherein said administering is by retrograde ductal administration.

24. The method of claim 18, wherein said administering is by injection.

25. The method of claim 18, wherein said administering is by cannulation.

26. The method of claim 25, wherein said cannulation is by inserting a cannula through a lumen of the gastrointestinal tract.

27. The method of claim 25, wherein said cannulation is through an external orifice.

28. The method of claim 25, wherein said cannulation is by inserting a cannula through a common bile duct, wherein the DNA construct is delivered directly into the hepatic duct and into the pancreatic duct.

29. The method of claim 18, wherein the introduced construct is expressed in each of the pancreas and the liver such that the level of polypeptide in pancreatic tissue is elevated relative to a level of polypeptide in pancreatic tissue after delivery of the same amount of the construct in the same manner to pancreas alone.

30. The method of claim 6, wherein the desired polypeptide is selected from the group consisting of insulin, growth hormone, interferon-alpha 2b, Interferon-alpha 2a, interferon-alpha N1, filgastim, insulinotropin, imiglucerase, clotting factor VIII, interferon-beta1b, erythropoietin, sargramostim, interleukin-2, interferon-gamma, anti-CD3 antibody, GPIIb/IIIa monoclonal antibody, adenosine deaminase, interleukin-8, insulin-like growth factor-1, platelet-derived growth factor, epidermal growth factor, and hemoglobin.

31. The method of claim 6, wherein the DNA of interest encodes a human insulin polypeptide.

* * * * *